(12) United States Patent
Griffin et al.

(10) Patent No.: US 7,498,305 B2
(45) Date of Patent: *Mar. 3, 2009

(54) ACTIVATED PROTEIN C VARIANTS WITH NORMAL CYTOPROTECTIVE ACTIVITY BUT REDUCED ANTICOAGULANT ACTIVITY

(75) Inventors: John H. Griffin, Del Mar, CA (US); Laurent O. Mosnier, San Diego, CA (US); Andrew J. Gale, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/886,766

(22) Filed: Jul. 8, 2004

(65) Prior Publication Data
US 2005/0037964 A1    Feb. 17, 2005

Related U.S. Application Data

(60) Provisional application No. 60/485,792, filed on Jul. 8, 2003.

(51) Int. Cl.
*A61K 38/36* (2006.01)
*C07K 14/745* (2006.01)
*C12N 9/48* (2006.01)
*C12P 21/02* (2006.01)

(52) U.S. Cl. .................. 514/12; 530/380; 435/212; 435/69.6; 424/94.5

(58) Field of Classification Search .................. 514/12; 530/380; 435/212, 69.6
See application file for complete search history.

(56) References Cited

U.S. PATENT DOCUMENTS 4,775,624 A    10/1988    Bang et al.

(Continued)

OTHER PUBLICATIONS

Gerlitz et al., "Mutation of protease domain residues Lys37-39 in human protein C inhibits activation by the thrombomodulin-thrombin complex without affecting activation by free thrombin," J Biol Chem 271(37):22285-22288, 1996.*

(Continued)

*Primary Examiner*—Rebecca E. Prouty
*Assistant Examiner*—Rosanne Kosson
(74) *Attorney, Agent, or Firm*—Morgan & Finnegan, L.L.P.

(57) ABSTRACT

Variants (mutants) of recombinant activated protein C (APC) or recombinant protein C (prodrug, capable of being converted to APC) that have substantial reductions in anticoagulant activity but that retain normal levels of anti-apoptotic activity are provided. Two examples of such recombinant APC mutants are KKK191-193AAA-APC and RR229/230M-APC. APC variants and prodrugs of the invention have the desirable property of being cytoprotective (anti-apoptotic effects), while having significantly reduced risk of bleeding. The invention also provides a method of using the APC variants or prodrugs of the invention to treat subjects who will benefit from APC's cytoprotective activities that are independent of APC's anticoagulant activity. These subjects include patients at risk of damage to blood vessels or tissue in various organs caused, at least in part, by apoptosis. At risk patients include, for example, those suffering (severe) sepsis, ischemia/reperfusion injury, ischemic stroke, acute myocardial infarction, acute or chronic neurodegenerative diseases, or those undergoing organ transplantation or chemotherapy, among other conditions. Methods of screening for variants of recombinant protein C or APC that are useful in accordance with the invention are also provided.

21 Claims, 7 Drawing Sheets

U.S. PATENT DOCUMENTS

| | | | |
|---|---|---|---|
| 4,981,952 | A | 1/1991 | Yan |
| 5,084,274 | A | 1/1992 | Griffin et al. |
| 6,037,322 | A * | 3/2000 | Grinnell et al. ............... 514/8 |
| 6,130,201 | A * | 10/2000 | Croce et al. .................... 514/7 |
| 7,204,981 | B2 | 4/2007 | Ciaccia et al. |
| 2003/0073632 | A1 | 4/2003 | Ciaccia et al. |
| 2007/0042961 | A1 | 2/2007 | Griffin et al. |
| 2007/0142272 | A1 | 6/2007 | Zlokovic et al. |

OTHER PUBLICATIONS

Riewald et al., "Activation of endothelial cell protease activated receptor 1 by the protein C pathway," Science 296:1880-1882, 2002.*

Mosnier et al., "Inhibition of staurosporine-induced apoptosis of endothelial cells by activated protein C requires protease-activated receptor-1 and endothelial cell protein C receptor," Biochem J 373:65-70, 2003.*

Weiss et al., "Rapid mapping of protein functional epitopes by combinatorial alanine scanning," PNAS 97(16):8950-8954, 2000.*

Gerlitz et al, "Mutation of protease domain residues Llys37-39 in human protein C inhibits activation by the thrombomodulin-thrombin complex without affecting activation by free thrombin." *J Biol. Chem.* vol. 271, No. 37, pp. 22285-22288, Sep. 13, 1996.

Riewald et al, "Activation of endothelial cell protease activated receptor 1 by the protein C pathway," *Science*, vol. 296, pp. 1880-1882, Jun. 7, 2002.

Abraham et al., "Assessment of the safety of recombinant tissue factor pathway inhibitor in patients with severe sepsis: a multicenter, randomized, placebo-controlled, single-blind, dose escalation study", *Crit. Care Med.*, 29:2081-2089 (2001).

Arosio et al., "Mutation of W215 compromises thrombin cleavage of fibrinogen, but not of PAR-1 or protein C", *Biochemistry*, 39:8095-8101 (2000).

Bernard et al., "Safety and dose relationship of recombinant human activated protein C for coagulopathy in severe sepsis", *Crit. Care Med.*, 29:2051-2059 (2001).

Bernard et al., "Efficacy and safety of recombinant human activated protein C for severe sepsis", *New Engl. J. Med.*, 344:699-709 (2001).

Chase and Shaw, "p-Nitrophenyl-p'-guanidinobenzoate HCI: a new active site titrant for trypsin", *Biochem. Biophys. Res. Commun.*, 29:508-514 (1967).

Cheng et al., "Activated protein C blocks p53-mediated apoptosis in ischemic human brain endothelium and is neuroprotective", *Nat. Med.*, 9:338-342 (2003).

Conway et al., "The lectin-like domain of thrombomodulin confers protection from neutrophil-mediated tissue damage by suppressing adhesion molecule expression via nuclear factor kappaB and mitogen-activated protein kinase pathways", *J. Exp. Med.*, 196:565-577 (2002).

Domotor et al., "Activated protein C alters cytosolic calcium flux in human brain endothelium via binding to endothelial protein C receptor and activation of protease activated receptor-1.", *Blood*, 101:4797-4801 (2003).

Edgell et al., "Permanent cell line expressing human factor VIII-related antigen established by hybridization", *Proc. Nat'l Acad. Sci., USA*, 80:3734-3737 (1983).

Esmon, "The anticoagulant and anti-inflammatory roles of the protein C anticoagulant pathway", *J. Autoimmun.*, 15:113-116 (2000).

Esmon, "Regulation of blood coagulation", *Biochim. Biophys. Acta.*, 1477:349-360 (2000).

Esmon, "The endothelial cell protein C receptor", *Thromb Haemost*, 83:639-643 (2000).

Esmon, "Protein C pathway in sepsis", *Ann. Med.*, 34:598-605, (2002).

Fernandez et al., "Recombinant murine-activated protein C is neuroprotective in a murine ischemic stroke model", *Blood Cells Mol. Dis.*, 30:271-276 (2003).

Fisher et al., "Models of the serine protease domain of the human antithrombotic plasma factor activated protein C and its zymogen", *Protein Science*, 3:588-599 (1994).

Friedrich et al., "Secondary substrate-binding exosite in the serine protease domain of activated protein C important for cleavage at Arg-506 but not at Arg-306 in factor Va", *J. Biol. Chem.*, 276:23105-23108 (2001).

Friedrich et al., "Structural and energetic characteristics of the heparin-binding site in antithrombotic protein C", *J. Biol. Chem.*, 276:24122-24128 (2001).

Fukodome and Esmon, "Molecular cloning and expression of murine and bovine endothelial cell protein C/activated protein C receptor (EPCR). The structural and functional conservation in human, bovine, and murine EPCR", *J. Biol. Chem.*, 270:5571-5577 (1995).

Gale et al., "Nonenzymatic anticoagulant activity of the mutant serine protease Ser360Ala-activated protein C mediated by factor Va", *Protein Sci.*, 6:132-140 (1997).

Gale et al., "The autolysis loop of activated protein C interacts with factor Va and differentiates between the Arg506 and Arg306 cleavage sites", *Blood*, 96:585-593 (2000).

Gale et al., "Molecular characterization of an extended binding site for coagulation factor Va in the positive exosite of activated protein C", *J. Biol. Chem.*, 277:28836-28840 (2002).

Griffin et al., "Activated protein C: potential therapy for severe sepsis, thrombosis, and stroke", *Semin. Hematol*, 39:197-205 (2002).

Griffin et al., "Activated protein C", *J. Thromb. Haemost.*, 5:73-80 (2007).

Haley et al., "The activation of bovine protein C by factor Xa", *J. Biol. Chem.*, 264:16303-16310 (1989).

Heeb et al., "Inhibition of activated protein C by recombinant alpha 1-antitrypsin variants with substitution of arginine or leucine for methionine358", *J. Biol. Chem.*, 265:2365-2369 (1990).

Hinds, "Treatment of sepsis with activated protein C", *Brit. Med. J.*, 323:881-882 (2001).

Idziorek et al., "YOPRO-1 permits cytofluorometric analysis of programmed cell death (apoptosis) without interfering with cell viability", *J. Immunol. Methods*, 185:249-258 (1995).

Isobe et al., "Activated protein C prevents endotoxin-induced hypotension in rats by inhibiting excessive production of nitric oxide", *Circulation*, 104:1171-1175 (2001).

Joyce et al., "Gene expression profile of antithrombotic protein c defines new mechanisms modulating inflammation and apoptosis", *J. Biol. Chem.*, 276:11199-11203 (2001).

Kalafatis and Mann, "Role of the membrane in the inactivation of factor Va by activated protein C", *J. Biol. Chem.*, 268:27246-27257 (1993).

Kanji et al., "Recombinant human activated protein C, drotrecogin alfa (activated): a novel therapy for severe sepsis", *Pharmacother.*, 21:1389-1402 (2001).

Kerschen, et al., "Endotoxemia and sepsis mortality reduction by non-anticoagulant activated protein C", *J. Exp. Med.*, 204:2439-2448 (2007).

Kisiel, "Human plasma protein C: isolation, characterization, and mechanism of activation by alpha-thrombin", *J. Clin. Invest.*, 64:761-769 (1979).

Knobe et al., "Probing the activation of protein C by the thrombin-thrombomodulin complex using structural analysis, site-directed mutagenesis, and computer modeling", *Proteins*, 35:218-234 (1999).

Kuliopulos et al., "Plasmin desensitization of the PAR1 thrombin receptor: kinetics, sites of truncation, and implications for thrombolytic therapy", *Biochemistry*, 38:4572-4585 (1999).

Marlar et al., "Mechanism of action of human activated protein C, a thrombin-dependent anticoagulant enzyme", *Blood*, 59:1067-1072 (1982).

Mather et al., "The 2.8 A crystal structure of Gla-domainless activated protein C", *EMBO J.*, 15:6822-6831 (1996).

Mesters et al., "Identification of a sequence of human activated protein C (residues 390-404) essential for its anticoagulatn activity", *J. Biol. Chem.*, 266:24514-24519 (1991).

Mosnier et al., "Activated protein C variants with normal cytoprotective but reduced anticoagulant activity", *Blood*, 104:1740-1744 (2004).

Mosnier et al., "The cytoprotective protein C pathway", *Blood*, 109:3161-3172 (2007).

Mosnier et al., "Activated protein C mutant with minimal anticoagulant activity, normal cytoprotective activity, and preservation of thrombin activable fibrinolysis inhibitor-dependent cytoprotective functions", *J. Biol. Chem.*, 282:33022-33033 (2007).

Nicolaes, et al., "Peptide bond cleavages and loss of functional activity during inactivation of factor Va and factor VaR506Q by activated protein C", *J. Biol. Chem.*, 270:21158-21166 (1995).

Norstrom et al., "Importance of protein S and phospholipid for activated protein C-mediated cleavages in factor Va", *J. Biol. Chem.*, 278:24904-24911 (2003).

Oganesyan et al., "The crystal structure of the endothelial protein C receptor and a bound phospholipid", *J. Biol. Chem.*, 277:24851-24854 (2002).

Regan et al., "The endothelial cell protein C receptor. Inhibition of activated protein C anticoagulant function without modulation of reaction with proteinase inhibitors", *J. Biol. Chem.*, 271:17499-17503 (1996).

Rosing and Tans, "Coagulation factor V: an old star shines again", *J. Thromb. Haemost.*, 78:427-433 (1997).

Rothbarth et al., "One single mRNA encodes the centrosomal protein CCD41 and the endothelial cell protein C receptor (EPCR)", *FEBS Lett.*, 458:77-80 (1999).

Sadowski et al., "Vitamin K-dependent carboxylase. Requirements of the rat liver microsomal enzyme system.", *J. Biol. Chem.*, 251:2770-2776 (1976).

Shen et al., "Involvement of Lys 62(217) and Lys 63(218) of human anticoagulant protein C in heparin stimulation of inhibition by the protein C inhibitor", *J. Thromb. Haemost.*, 82:72-79 (1999).

Shu et al., "Activated protein C suppresses tissue factor expression on U937 cells in the endothelial protein C receptor-dependent manner", *FEBS Lett.* 477:208-212 (2000).

Stearns-Kurosawa, et al., "The endothelial cell protein C receptor augments protein C activation by the thrombin-thrombomodulin complex", *Proc. Nat'l Acad. Sci., USA*, 93:10212-10216 (1996).

Taylor et al., "The endothelial cell protein C receptor aids in host defense against *Escherichia coli* sepsis", *Blood*, 95:1680-1686 (2000).

Theofilopoulos, "Systemic lupus erythematosus (SLE), Experimental models", *Encyclopedia of Immunology*, pp. 1414-1417 (1992).

Warren et al., "High-dose antithrombin III in severe sepsis: a randomized controlled trial", *JAMA*, 286:1869-1878 (2001).

Yan et al., "Characterization and novel purification of recombinant human protein C from three mammalian cell lines", *Biotechnology*, 8:655-661 (1990).

Yednock et al., "Prevention of experimental autoimmune encephalomyelitis by antibodies against alpha 4 beta 1 integrin", *Nature* 356:63-66 (1992).

GenBank accession P04070 (as accessed via the NCBI webpage http://www.ncbi.nlm.nih.gov/entrez/viewer.fcgi?db=protein&id=131067 on Oct. 2, 2008), record dated Jun. 10, 2008.

* cited by examiner

SEQUENCE LISTING

<160> NUMBER OF SEQ ID NOS: 15

<210> SEQ ID NO 1

-continued

```
<211> LENGTH: 10
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(10)
<223> OTHER INFORMATION: PAR-1 agonist peptide

<400> SEQUENCE: 1

Thr Phe Leu Leu Arg Asn Pro Asn Asp Lys
1               5                   10

<210> SEQ ID NO 2
<211> LENGTH: 11
<212> TYPE: PRT
<213> ORGANISM: human
<220> FEATURE:
<221> NAME/KEY: MISC_FEATURE
<222> LOCATION: (1)..(11)
<223> OTHER INFORMATION: Corresponds to residues 225-235 in the
      full-length wt-APC protein

<400> SEQUENCE: 2

Glu Tyr Asp Leu Arg Arg Trp Glu Lys Trp Glu
1               5                   10

<210> SEQ ID NO 3
<211> LENGTH: 11
<212> TYPE: PRT
<213> ORGANISM: human
<220> FEATURE:
<221> NAME/KEY: MISC_FEATURE
<222> LOCATION: (5)..(6)
<223> OTHER INFORMATION: Residues 5-6 are R-to-A mutations corresponding
      to residues 229-230 in the full-length wt-APC protein

<400> SEQUENCE: 3

Glu Tyr Asp Leu Ala Ala Trp Glu Lys Trp Glu
1               5                   10

<210> SEQ ID NO 4
<211> LENGTH: 6
<212> TYPE: PRT
<213> ORGANISM: human
<220> FEATURE:
<221> NAME/KEY: MISC_FEATURE
<222> LOCATION: (1)..(6)
<223> OTHER INFORMATION: Corresponds to residues 189-194 in the
      full-length wt-APC protein

<400> SEQUENCE: 4

Asp Ser Lys Lys Lys Leu
1               5

<210> SEQ ID NO 5
<211> LENGTH: 6
<212> TYPE: PRT
<213> ORGANISM: human
<220> FEATURE:
<221> NAME/KEY: MISC_FEATURE
<222> LOCATION: (3)..(5)
<223> OTHER INFORMATION: Residues 3-5 are K-to-A mutations corresponding
      to residues 191-193 in the full-length wt-APC protein

<400> SEQUENCE: 5

Asp Ser Ala Ala Ala Leu
1               5
```

```
<210> SEQ ID NO 6
<211> LENGTH: 11
<212> TYPE: PRT
<213> ORGANISM: human
<220> FEATURE:
<221> NAME/KEY: MISC_FEATURE
<222> LOCATION: (1)..(11)
<223> OTHER INFORMATION: Corresponds to residues 305-315 in the
      full-length wt-APC protein

<400> SEQUENCE: 6

Ser Arg Glu Lys Glu Ala Lys Arg Asn Arg Thr
1               5                   10

<210> SEQ ID NO 7
<211> LENGTH: 11
<212> TYPE: PRT
<213> ORGANISM: human
<220> FEATURE:
<221> NAME/KEY: MISC_FEATURE
<222> LOCATION: (2)..(2)
<223> OTHER INFORMATION: Residue 2 is a R-to-A mutation corresponding to
      position 306 in the full-length wt-APC protein
<220> FEATURE:
<221> NAME/KEY: MISC_FEATURE
<222> LOCATION: (7)..(7)
<223> OTHER INFORMATION: Residue 7 is a K-to-A mutation corresponding to
      position 311 in the full-length wt-APC protein
<220> FEATURE:
<221> NAME/KEY: MISC_FEATURE
<222> LOCATION: (8)..(8)
<223> OTHER INFORMATION: Residue 8 is a R-to-A mutation corresponding to
      position 312 in the full-length wt-APC protein
<220> FEATURE:
<221> NAME/KEY: MISC_FEATURE
<222> LOCATION: (10)..(10)
<223> OTHER INFORMATION: Residue 10 is a R-to-A mutation corresponding
      to position 314 in the full-length wt-APC protein

<400> SEQUENCE: 7

Ser Ala Glu Lys Glu Ala Ala Ala Asn Ala Thr
1               5                   10

<210> SEQ ID NO 8
<211> LENGTH: 30
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(30)
<223> OTHER INFORMATION: Corresponds to residues 33-62 of the PAR-1
      sequence

<400> SEQUENCE: 8

Ala Thr Asn Ala Thr Leu Asp Pro Arg Ser Phe Leu Leu Arg Asn Pro
1               5                   10                  15

Asn Asp Lys Tyr Glu Pro Phe Trp Glu Asp Glu Glu Lys Asn
            20                  25                  30

<210> SEQ ID NO 9
<211> LENGTH: 6
<212> TYPE: PRT
<213> ORGANISM: human
<220> FEATURE:
<221> NAME/KEY: MISC_FEATURE
```

```
<222> LOCATION: (1)..(6)
<223> OTHER INFORMATION: Corresponds to residues 227-232 in the
      full-length wt-APC protein

<400> SEQUENCE: 9

Asp Leu Arg Arg Trp Glu
1               5

<210> SEQ ID NO 10
<211> LENGTH: 6
<212> TYPE: PRT
<213> ORGANISM: human
<220> FEATURE:
<221> NAME/KEY: MISC_FEATURE
<222> LOCATION: (3)..(4)
<223> OTHER INFORMATION: Residues 3-4 are R-to-A mutations corresponding
      to residues 229-230 in the full-length wt-APC protein

<400> SEQUENCE: 10

Asp Leu Ala Ala Trp Glu
1               5

<210> SEQ ID NO 11
<211> LENGTH: 7
<212> TYPE: PRT
<213> ORGANISM: human
<220> FEATURE:
<221> NAME/KEY: MISC_FEATURE
<222> LOCATION: (1)..(7)
<223> OTHER INFORMATION: Corresponds to residues 189-195 in the
      full-length wt-APC protein

<400> SEQUENCE: 11

Asp Ser Lys Lys Lys Leu Ala
1               5

<210> SEQ ID NO 12
<211> LENGTH: 7
<212> TYPE: PRT
<213> ORGANISM: human
<220> FEATURE:
<221> NAME/KEY: MISC_FEATURE
<222> LOCATION: (3)..(5)
<223> OTHER INFORMATION: Residues 3-5 are K-to-A mutations corresponding
      to residues 191-193 in the full-length wt-APC protein

<400> SEQUENCE: 12

Asp Ser Ala Ala Ala Leu Ala
1               5

<210> SEQ ID NO 13
<211> LENGTH: 5
<212> TYPE: PRT
<213> ORGANISM: human
<220> FEATURE:
<221> NAME/KEY: MISC_FEATURE
<222> LOCATION: (1)..(5)
<223> OTHER INFORMATION: Corresponds to residues 358-362 in the
      full-length wt-APC protein

<400> SEQUENCE: 13

Gly Asp Ser Gly Gly
1               5

<210> SEQ ID NO 14
<211> LENGTH: 5
<212> TYPE: PRT
<213> ORGANISM: human
<220> FEATURE:
```

```
<221> NAME/KEY: MISC_FEATURE
<222> LOCATION: (3)..(3)
<223> OTHER INFORMATION: Residue 3 is a S-to-A mutation corresponding to
      position 360 in the full-length wt-APC protei
<220> FEATURE:
<221> NAME/KEY: MISC_FEATURE
<222> LOCATION: (3)..(3)
<223> OTHER INFORMATION: Residue 3 is a S-to-A mutation corresponding to
      position 360 in the full-length wt-APC protein

<400> SEQUENCE: 14

Gly Asp Ala Gly Gly
1               5

<210> SEQ ID NO 15
<211> LENGTH: 419
<212> TYPE: PRT
<213> ORGANISM: Human

<400> SEQUENCE: 15
```

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

```
Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
                340                 345                 350

Gln Asp Ala Cys Glu Gly Asp Ser Gly Gly Pro Met Val Ala Ser Phe
            355                 360                 365

His Gly Thr Trp Phe Leu Val Gly Leu Val Ser Trp Gly Glu Gly Cys
        370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro
```

ACTIVATED PROTEIN C VARIANTS WITH NORMAL CYTOPROTECTIVE ACTIVITY BUT REDUCED ANTICOAGULANT ACTIVITY

This invention claims the benefit of provisional application Ser. No. 60/485,792, filed Jul. 8, 2003, under 35 U.S.C §119(e), the entire disclosure of which is incorporated herein by reference.

"This invention was made with the U.S. Government support under Contract No. HL52246 by the National Institutes of Health. The U.S. Government has certain rights to this invention."

FIELD OF THE INVENTION

The present invention relates to variants (mutants) of recombinant protein C and activated protein C, an enzyme that normally has anti-thrombotic, anti-inflammatory, and anti-apoptotic activities. The recombinant activated protein C mutants of the invention have markedly reduced anticoagulant activity, but retain near normal anti-apoptotic (cytoprotective) activity, so that the ratio of anti-apoptotic to anticoagulant activity is greater in the variants than it is in wild-type or endogenous activated protein C. This invention also relates to methods of using these variants. The activated protein C variants of the invention are useful as inhibitors of apoptosis or cell death and/or as cell survival factors, especially for cells or tissues of the nervous system, which are stressed or injured. The invention further relates to therapeutic use of the variants of this invention in subjects at risk for cell damage caused at least in part by apoptosis, and to therapeutic compositions comprising such mutant proteins, which compositions should provide the desired cytoprotective benefits while carrying a lower risk of bleeding, a side effect of activated protein C therapy.

BACKGROUND OF THE INVENTION

Protein C is a member of the class of vitamin K-dependent serine protease coagulation factors. Protein C was originally identified for its anticoagulant and profibrinolytic activities. Protein C circulating in the blood is an inactive zymogen that requires proteolytic activation to regulate blood coagulation through a complex natural feedback mechanism. Human protein C is primarily made in the liver as a single polypeptide of 461 amino acids. This precursor molecule is then post-translationally modified by (i) cleavage of a 42 amino acid signal sequence, (ii) proteolytic removal from the one-chain zymogen of the lysine residue at position 155 and the arginine residue at position 156 to produce the two-chain form (i.e., light chain of 155 amino acid residues attached by disulfide linkage to the serine protease-containing heavy chain of 262 amino acid residues), (iii) carboxylation of the glutamic acid residues clustered in the first 42 amino acids of the light chain resulting in nine gamma-carboxyglutamic acid (Gla) residues, and (iv) glycosylation at four sites (one in the light chain and three in the heavy chain). The heavy chain contains the serine protease triad of Asp257, His211 and Ser360.

Similar to most other zymogens of extracellular proteases and the coagulation factors, protein C has a core structure of the chymotrypsin family, having insertions and an N-terminus extension that enable regulation of the zymogen and the enzyme. Of interest are two domains with amino acid sequences similar to epidermal growth factor (EGF). At least a portion of the nucleotide and amino acid sequences for protein C from human, monkey, mouse, rat, hamster, rabbit, dog, cat, goat, pig, horse, and cow are known, as well as mutations and polymorphisms of human protein C (see GenBank accession P04070). Other variants of human protein C are known which affect different biological activities.

Activation of protein C is mediated by thromblin, acting at the site between the arginine residue at position number 15 of the heavy chain and the leucine residue at position 16 (chymotrypsin numbering) (See Kisiel, J. Clin. Invest., 64:761-769, 1976; Marlar et al., Blood, 59:1067-1072, 1982; Fisher et al. Protein Science, 3:588-599, 1994). Other proteins including Factor Xa (Haley et al., J. Biol. Chem., 264:16303-16310, 1989), Russell's viper venom, and trypsin (Esmon et al., J. Biol. Chem., 251:2770-2776, 1976) also have been shown to enzymatically cleave and convert inactive protein C to its activated form.

Thrombin binds to thrombomodulin, a membrane-bound thrombin receptor on the luminal surface of endothelial cells, thereby blocking the procoagulant activity of thrombin via its exosite I, and enhancing its anticoagulant properties, i.e., activating protein C. As an anticoagulant, activated protein C (APC), aided by its cofactor protein S, cleaves the activated cofactors factor Va and factor VIIa, which are required in the intrinsic coagulation pathway to sustain thrombin formation (Esmon et al., Biochim. Biophys. Acta., 1477:349-360, 2000a), to yield the inactivated cofactors factor Vi and factor VIIIi.

The thrombin/thrombomodulin complex mediated activation of protein C is facilitated when protein C binds to the endothelial protein C receptor (EPCR), which localizes protein C to the endothelial cell membrane surface. When complexed with EPCR, APC's anticoagulant activity is inhibited; APC expresses its anticoagulant activity when it dissociates from EPCR, especially when bound to negatively charged phospholipids on activated platelet or endothelial cell membranes.

Components of the protein C pathway contribute not only to anticoagulant activity, but also to anti-inflammatory functions (Griffin et al., Sem. Hematology, 39:197-205, 2002). The anti-inflammatory effects of thrombomodulin, recently attributed to its lectin-like domain, can protect mice against neutrophil-mediated tissue damage (Conway et al., J. Exp. Med. 196:565-577, 2002). The murine centrosomal protein CCD41 or centrocyclin, involved in cell-cycle regulation is identical to murine EPCR lacking the first N-terminal 31 amino acids (Rothbarth et al., FEBS Lett., 458:77-80, 1999; Fukodome and Esmon, J. Biol. Chem., 270:5571-5577, 1995). EPCR is structurally homologous to the MHC class 1/CD1 family of proteins, most of which are involved in inflammatory processes. This homology suggests that the function of EPCR may not be limited to its ability to localize APC or protein C on the endothelial membrane (Oganesyan et al., J. Biol. Chem., 277:24851-24854, 2002). APC provides EPCR-dependent protection against the lethal effects of E.coli infusion in baboons (Taylor et al., Blood, 95:1680-1686, 2000) and can downregulate proinflammatory cytokine production and favorably alter tissue factor expression or blood pressure in various models (Shu et al., FEBS Lett. 477:208-212, 2000; Isobe et al., Circulation, 104:1171-1175, 2001; Esmon, Ann. Med., 34:598-605, 2002).

Inflammation is the body's reaction to injury and infection. Three major events are involved in inflammation: (1) increased blood supply to the injured or infected area; (2) increased capillary permeability enabled by retraction of endothelial cells; and (3) migration of leukocytes out of the capillaries and into the surrounding tissue (hereinafter referred to as cellular infiltration) (Roitt et al., Immunology, Grower Medical Publishing, New York, 1989).

Many serious clinical conditions involve underlying inflammatory processes in humans. For example, multiple sclerosis (MS) is an inflammatory disease of the central nervous system. In MS, circulating leukocytes infiltrate inflamed brain endothelium and damage myelin, with resultant impaired nerve conduction and paralysis (Yednock et al., Nature 366:63-66 (1992)). Systemic lupus erythematosus (SLE) is an autoimmune disease characterized by the presence of tissue damage caused by self antigen directed antibodies. Auto-antibodies bound to antigens in various organs lead to complement-mediated and inflammatory cell mediated tissue damage (Theofilopoulos, A.N., Encyclopedia of Immunology, pp. 1414-1417 (1992)).

APC has not only anticoagulant and anti-inflammatory activities but also anti-apoptotic activity. EPCR has been found to be a required cofactor for the anti-apoptotic activity of APC in certain cells, as APC activation of protease activated receptor-1 (PAR-1) is EPCR-dependent (Riewald et al., Science, 2296:1880-1882, 2002; Cheng et al., Nat. Med., 9:338-342, 2003; Mosnier and Griffin, Biochem. J., 373:65-70, 2003). APC also has been shown potentially to inhibit staurosporine-induced apoptosis in endothelial cells in vitro by modulating the expression of NFκB subunits (Joyce et al., J. Biol. Chem., 276:11199-11203, 2001). Staurosporine-induced apoptosis in human umbilical vein endothelial cells (HUVEC) and tumor necrosis factor-α-mediated injury of HUVEC, based on transcriptional profiling, suggest that APC's inhibition of NFκB signaling causes down regulation of adhesion molecules (Joyce et al., supra, 2001). APC's induction of anti-apoptotic genes (e.g., Bcl2-related protein A1 or Bcl2A1, inhibitor of apoptosis 1 or cIAP1, endothelial nitric oxide synthase or eNOS) has been interpreted as a possible mechanism linked to APC's anti-apoptotic effects in a staurosporine model of apoptosis.

APC has a remarkable ability to reduce all-cause 28-day mortality by 19% in patients with severe sepsis (Bernard et al., New Engl. J. Med. 344:699-709, 2001a), whereas, potent anticoagulant agents such as antithrombin III and recombinant TFPI have failed in similar phase III clinical trials (Warren et al., JAMA, 286:1869-1878, 2001; Abraham et al., Crit. Care Med., 29:2081-2089). The explanation for this difference may lie in the recently described anti-apoptotic activity of APC, as well as its anti-inflammatory activity. The clinical success of APC in treating sepsis may be related to its direct cellular effects that mediate its anti-apoptotic or anti-inflammatory activity.

In spite of the numerous in vivo studies documenting the beneficial effects of APC, there is limited information about the molecular mechanisms responsible for APC's direct anti-inflammatory and anti-apoptotic effects on cells. APC can directly modulate gene expression in human umbilical vein endothelial cells (HUVEC) with notable effects on anti-inflammatory and cell survival genes (Joyce et al., supra, 2001; Riewald et al., supra, 2002). Riewald et al. have shown this direct effect of APC on certain cells requires PAR-1 and EPCR (Riewald et al., supra, 2002), although they provided no data that related APC functional activity with PAR-1-signaling.

Recombinant activated protein C (rAPC), similar to Xigris (Eli Lilly & Co.), is approved for treating severe sepsis and it may eventually have other beneficial applications. However, clinical studies have shown APC treatment to be associated with increased risk of serious bleeding. This increased risk of bleeding presents a major limitation of APC therapy. If APC's effects in sepsis can be attributed to its anti-inflammatory and cell survival activities, a compound that retains the beneficial anti-apoptotic or cytoprotective activity but has a less anticoagulant activity is desirable.

SUMMARY OF THE INVENTION

It is an object of this invention to provide variants (mutants) of recombinant APC and prodrugs (e.g., variants of recombinant protein C) as therapeutics or research tools for use in alleviating or preventing cell damage associated at least in part with apoptosis. It is also an object of this invention to provide a method of alleviating or preventing cell damage associated at least in part with apoptosis, especially in subjects at risk for or suffering from such cell damage. Another object of this invention is to provide a means for screening candidate mutants for use in accordance with the invention.

The invention is directed to variants of recombinant APC and prodrugs (protein C variants) that provide reduced anticoagulant activity relative to anti-apoptotic activity compared to wild-type, and, therefore, have use as cytoprotective agents. Two examples of such recombinant APC mutants are KKK191-193AAA-APC (mutation of lysines 191, 192 and 193 to alanines) and RR229/230AA-APC (mutation of arginines 229 and 230 to alanines). As we demonstrate herein, these exemplary APC variants retain the desirable property of normal anti-apoptotic, cytoprotective activity but provide significantly reduced risk of bleeding, given their reduced anticoagulant activity. The APC and protein C variants of the invention provide a ratio of anti-apoptotic to anticoagulant activity greater than that of wild-type APC (i.e., >1.0).

In one embodiment of the invention, a method of preventing or alleviating damage associated at least in part with apoptosis is provided. In a related aspect of this embodiment, a method of treating subjects at risk for cell damage associated at least in part with apoptosis is provided. These subjects include patients at risk of damage to blood vessels or tissue in various organs caused, at least in part, by apoptosis. At risk patients include, for example, those suffering (severe) sepsis, ischemia/reperfusion injury, ischemic stroke, acute myocardial infarction, acute or chronic neurodegenerative diseases, or those undergoing organ transplantation or chemotherapy, among other conditions. The APC variants and prodrugs of the invention should be useful in treating subjects who will benefit from APC protective activities that are independent of APC's anticoagulant activity. Prodrug embodiments of this invention may involve recombinant protein C variants that, following conversion of protein C to APC, exhibit reduced anticoagulant activity while retaining normal or near-normal cell protective activities. For example, variants of protein C, when activated, will have the desired ratio of anti-apoptotic to anticoagulant activity of greater than 1.0.

In another embodiment of the invention, the APC mutants may be provided as therapeutics or in therapeutic compositions, to offer beneficial cytoprotective effects in cells, while carrying much less risk of bleeding. In yet another embodiment of the invention, methods of screening candidate recombinant APC variants having reduced anticoagulant activity, but retaining the beneficial cell protective and anti-inflammatory activities are provided.

Given the risk of bleeding associated with wild type activated protein C, the APC mutants of this invention offer advantages over currently available wild-type recombinant APC. Therefore, APC mutants of the invention are expected to provide superior therapy, either alone or adjunctive to other agents, whenever APC might be used for its anti-inflammatory or anti-apoptotic (cell survival) activities, rather than purely for its anticoagulant activity.

DESCRIPTION OF DRAWINGS

FIG. 1a: dose-dependent reduction in STS-induced apoptosis expressed as percent apoptotic cells. FIG. 1b: dose-dependent reduction in STS-induced apoptosis with data normalized as percent apoptotic cells relative to control STS (no APC).

DETAILED DESCRIPTION OF THE INVENTION

Figure 1A:
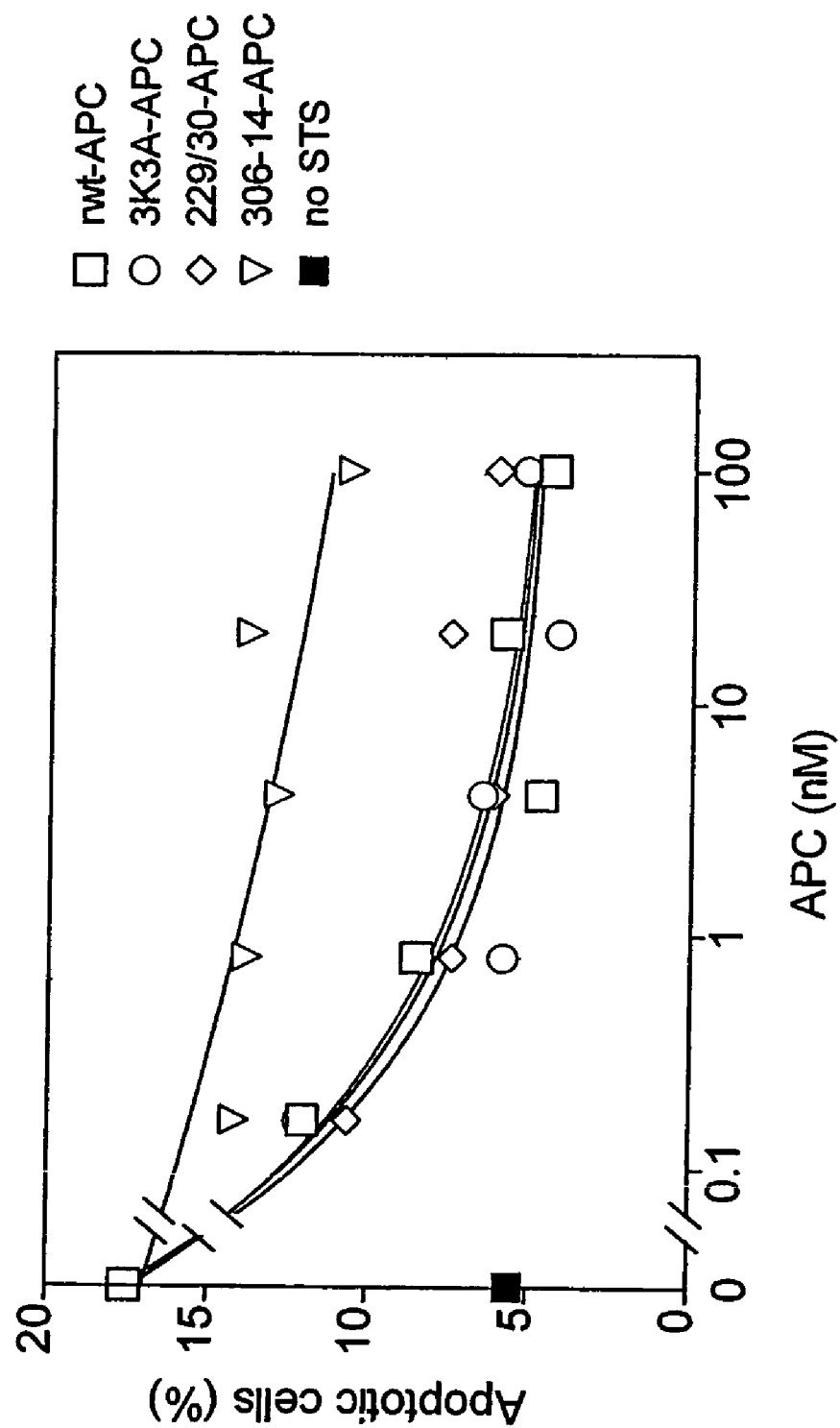
FIGS. 1a-1b: Inhibition of staurosporine-induced (STS) apoptosis in Eahy926 endothelial cells by wild-type (rwt-APC) and variants of recombinant APC.

Activated protein C (APC) has traditionally been regarded as an anticoagulant enzyme in the coagulation cascade, inhibiting thrombin formation and subsequent fibrin-clot formation by inactivating the cofactors factor Va and factor VIIIa (Esmon, supra, 2000a). However, APC also has the remarkable ability to reduce mortality in severe sepsis (Bernard et al., supra, 2001a; Bernard et al., Crit. Care Med., 29:2051-59, 2001b; Hinds, Brit. Med. J., 323:881-82, 2001; Kanji et al., Pharmacother., 21:1389-1402, 2001), while other anticoagulants such as antithrombin III and tissue factor pathway inhibitor have failed in this capacity (Warren et al., supra, 2001; Abraham et al., supra, 2001). This property of APC has peaked investigators' interest in the less extensively studied direct anti-inflammatory and anti-apoptotic activities attributed to APC (see, e.g., Cheng et al. Nat. Med., 9:338-42, 2003; Domotor et al., Blood, 101:4797-4801, 2003; Fernandez et al., Blood Cells Mol. Dis., 30:271-276, 2003; Esmon, J. Autoimmun., 15:113-116, 2000b). APC also has potential to protect the brain from damage caused by ischemic stroke (Cheng et al., supra, 2003; Esmon Thrombos Haemostas, 83:639-643, 2000c).

A major concern for the use of APC as a therapeutic is an increased risk of bleeding complications (Bernard et al., supra, 2001a; Bernard et al., supra, 2001b) due to APC anticoagulant activity. The APC variants of this invention solve this problem by having reduced anticoagulant activity over endogenous APC or wild-type recombinant APC, while retaining beneficial anti-apoptotic activity. Differentiating the anticoagulant activity from the anti-apoptotic activity was the first step in solving this problem. We have focused in part on the role of EPCR in regulation of these activities.

EPCR was originally discovered as a receptor capable of binding protein C and APC with equal affinities (Fukodome and Esmon, supra, 1995), and EPCR was shown to enhance the activation of protein C by the thrombin-thrombomodulin complex (Stearns-Kurosawa, et al., Proc. Nat'l Acad. Sci., USA, 93:10212-10216, 1996), apparently by optimizing the spatial localization of protein C for efficient activation by thrombomodulin-bound thrombin. Presumably EPCR binds APC to the endothelial surface and positions APC's active site proximate to the PAR-1 cleavage site at Arg41. Paradoxically, although EPCR function might be anticoagulant by stimulating protein C activation (Stearns-Kurosawa, et al., supra, 1996), APC anticoagulant activity is actually inhibited when APC is bound to EPCR (Regan et al., J. Biol. Chem., 271:17499-17503, 1996). Because binding of APC to EPCR is essential for APC's anti-apoptotic activity, we have concluded that the anti-apoptotic activity of APC is independent of its anticoagulant activity. We hypothesized that certain APC mutants could be generated which lack anticoagulant activity but retain anti-apoptotic activity. Such mutants could be therapeutically useful if they provided patients with direct cell survival activity without increased risks of bleeding.

We have determined the structural elements of APC required for its anti-apoptotic activity, by assaying different forms of APC for their anti-apoptotic activity. The staurosporine-induced apoptosis was blocked by pretreatment of APC with an anti-APC monoclonal antibody or heat denaturation of APC, thereby establishing the specificity of APC's anti-apoptotic activity (Mosnier and Griffin, supra, 2003). APC-mediated inhibition of staurosporine-induced apoptosis was found to require APC's active site, since the inactive protein C zymogen, as well as an inactive APC mutant, in which the active site Ser was replaced by Ala, S360A-APC (Gale et al., Protein Sci., 6:132-140, 1997), were devoid of anti-apoptotic activity (Mosnier and Griffin, supra, 2003). This implies that the anti-apoptotic activity of APC is mediated by proteolysis.

It was not known whether the APC-mediated inhibition of staurosporine-induced apoptosis (Joyce et al., supra, 2001) was dependent on PAR-1 and EPCR, until we demonstrated that inhibition of staurosporine-induced apoptosis by APC was dependent on PAR-1 and EPCR using a modified staurosporine-induced apoptosis model with EAhy926 endothelial cells (Mosnier and Griffin, supra, 2003). Inhibition of hypoxia-induced apoptosis in human brain endothelial cells also has been shown to require PAR-1 (Cheng et al., supra, 2003). Thus, consistent with the implication that APC's proteolytic active site is required for inhibition of apoptosis, preincubation of cells with blocking antibodies against PAR-1, but not against PAR-2, abolished APC-mediated inhibition of staurosporine-induced apoptosis (Mosnier and Griffin, supra, 2003). Furthermore, APC anti-apoptotic activity was abolished by an anti-EPCR antibody that blocks binding of APC to EPCR (Mosnier and Griffin, supra, 2003), and controls showed that this effect of the anti-EPCR antibody was neutralized by preincubation of the antibody with its peptide immunogen (Mosnier and Griffin, supra, 2003). Therefore, based on antibody blocking studies, PAR-1 and EPCR are required for APC to inhibit staurosporine-induced apoptosis of endothelial cells.

This requirement for PAR-1 and EPCR for inhibition of staurosporine-induced apoptosis of EAhy926 endothelial cells also is consistent with the finding that these receptors are important for APC's anti-apoptotic activity in the setting of hypoxic brain microvascular endothelial cells (Cheng et al., supra, 2003).

APC can cleave a synthetic extracellular N terminal PAR 1 polypeptide at Arg41, the thrombin cleavage site (Kuliopulos et al., Biochemistry, 38:4572-4585, 1999). Cleavage of this synthetic PAR 1 polypeptide by APC is 5,000-times slower than by thrombin (Kuliopulos et al., supra, 1999). When thrombin cleaves PAR 1 at Arg41, potent cell signaling pathways might be initiated. It is likely that APC cleavage of PAR 1 at Arg41 initiates cell signals, including phosphorylation of MAP kinase (Riewald et al., supra, 2002). In brain endothelial cells subjected to hypoxia, an early result of APC signaling is the inhibition of increases in the levels of p53 (Cheng et al., supra, 2003). Previous studies suggest that APC directly alters the gene expression profiles of HUVEC so that several anti-apoptotic genes are upregulated (Joyce et al., supra, 2001; Riewald et al., supra, 2002) and that APC specifically downregulates levels of the pro-apoptotic factor, Bax, while it upregulates levels of the anti-apoptotic factor, Bcl 2, in brain endothelial cells (Cheng et al., supra, 2003). The specific alteration of the critical ratio of Bax/Bcl 2 is likely of key importance for apoptosis. Other than these events, little can be stated about the mechanisms for PAR 1-dependent APC signaling. It is interesting to note that the PAR 1 agonist peptide, TFLLRNPNDK (SEQ ID. 1), exhibited no protection from staurosporine-induced apoptosis of EAhy926 cells whereas this agonist provided partial rescue of brain endothelial cells from hypoxia-induced apoptosis, suggesting there are subtle, but significant, differences between APC's PAR 1-dependent anti-apoptotic activities in these two models.

In vivo data are consistent with an important distinction between the anticoagulant and cell protective activities of APC. APC-induced neuroprotective effects in a murine ischemia/reperfusion injury model were observed at low APC doses that had no effect on fibrin deposition or on restoration of blood flow, indicating that APC's neuroprotective effects, at least in part, were independent of APC's anticoagulant activity (Cheng et al., supra, 2003).

No inhibition of staurosporine-induced apoptosis of EAhy926 cells was observed with either PAR-1 or PAR-2 agonist peptides in the absence of APC. Moreover, thrombin, the archetype activator of PAR-1, did not inhibit staurosporine-induced apoptosis (Mosnier and Griffin, supra, 2003). The failure of these other activators of PAR-1 to provide cell survival activity indicates that the PAR-1-dependent antiapoptotic effects of APC for staurosporine-induced apoptosis are specific for APC. Without being bound to a mechanism of action, we can speculate that when EPCR-bound APC cleaves and activates PAR-1, a significant modulation of PAR-1's intracellular signaling occurs, compared to signals triggered by thrombin or the PAR-1 agonist peptide. Another potential source of complexity may arise from the reported ability of EPCR to mediate nuclear translocation of APC (Esmon, supra, 2000c). The intracellular signals and pathways that cause inhibition of apoptosis by APC in various cell model systems remain to be elucidated.

The physiological relevance of APC EPCR-dependent signaling via PAR-1 is further demonstrated by the APC-induced neuroprotective effects in a murine ischemia/reperfusion injury model that requires PAR-1 and EPCR (Cheng et al., supra, 2003). APC may act via the EPCR and PAR-1 on stressed brain endothelial cells, or the PAR-1 and the protease activated receptor-3 (PAR-3) on stressed neurons, to activate anti-apoptotic pathways and/or pro-survival pathways in these stressed and/or injured brain cells. In human brain endothelium in vitro and in animals in vivo (ischemic stroke and NMDA models), APC can inhibit the p53-signaling proapoptotic pathway in stressed or injured brain cells (International Patent Application No. PCT/US03/38764).

EXAMPLES

Structure-activity relationships of protein C and activated protein C may be studied using variant polypeptides produced with an expression construct transfected in a host cell with or without expressing endogenous protein C. Thus, mutations in discrete domains of protein C or activated protein C may be associated with decreasing or even increasing activity in the protein's function.

To generate the APC variants and prodrugs of this invention, which provide a reduced risk of bleeding, i.e., reduced anticoagulant activity, but that retain useful cytoprotective activities, we have dissected anticoagulant activity from antiapoptotic activity of APC by site-directed mutagenesis. Several amino acids in various surface loops of the protease domain of APC were identified that, when mutated to alanine, severely reduced anticoagulant activity but did not affect anti-apoptotic activity. These unexpected findings indicate that strategies aimed at reducing the anticoagulant activity while preserving the anti-apoptotic activity of APC are feasible and worthwhile, because they are likely to reduce bleeding complications associated with the current and future clinical uses of recombinant APC variants which retain cytoprotective activities.

The structural basis of APC's anticoagulant activity has been centered primarily on the interaction of APC with factor Va. APC cleavage sites within factor Va are located at residues $Arg^{306}$, $Arg^{506}$ and $Arg^{679}$ and cleavage of the former two correlates with loss of cofactor activity (Rosing and Tans, Thromb Haemost, 78:427-433, 1997; Kalafatis and Mann, J.

Biol. Chem., 268:27246-57, 1993). Cleavage of factor Va at Arg$^{506}$ occurs rapidly and usually precedes cleavage at Arg$^{306}$. It is therefore considered the predominant site for the initial inactivation of the factor Va molecule (Norstrom et al., J. Biol. Chem., 278:24904-1133, 2003; Nicolaes, et al., J. Biol. Chem., 270:21158-66, 1995). The interaction of APC with the Arg$^{506}$ cleavage site in factor Va has been extensively characterized and as a result a factor Va binding site on the positively charged surface of the protease domain of APC has been defined (Gale et al., Blood, 96:585-593, 2000; Gale et al., J. Biol. Chem. 277:28836-28840, 2002; Friedrich et al., J. Biol. Chem., 276:23105-08, 2001a; Knobe et al., Proteins, 35:L218-234, 1999; Shen et al., Thromb. Haemost., 82:72-79, 1999). This positive exosite for factor Va binding on APC is generally located in the same area as the anion binding exosite I of thrombin and is comprised of residues in loop 37, which contains protein C residues 190-193 (equivalent to chymotrypsin (CHT) residues 36-39), the calcium ion-binding loop containing residues 225-235 (CHT 70-80) and the autolysis loop containing residues 301-316 (CHT 142-153) (Mather et al., EMBO J., 15:6822-31, 1996). In addition, mutations in loop 60, containing protein C residues 214-222 (CHT 60-68) have little effect on factor Va inactivation by APC although this loop is implicated in interactions with thrombomodulin and heparin (Gale et al., supra, 2002; Friedrich et al., supra, 2001a; Knobe et al., supra, 1999; Shen et al., supra, 1999; Friedrich et al., J. Biol. Chem., 276:24122-28, 2001b).

Figure 1B:
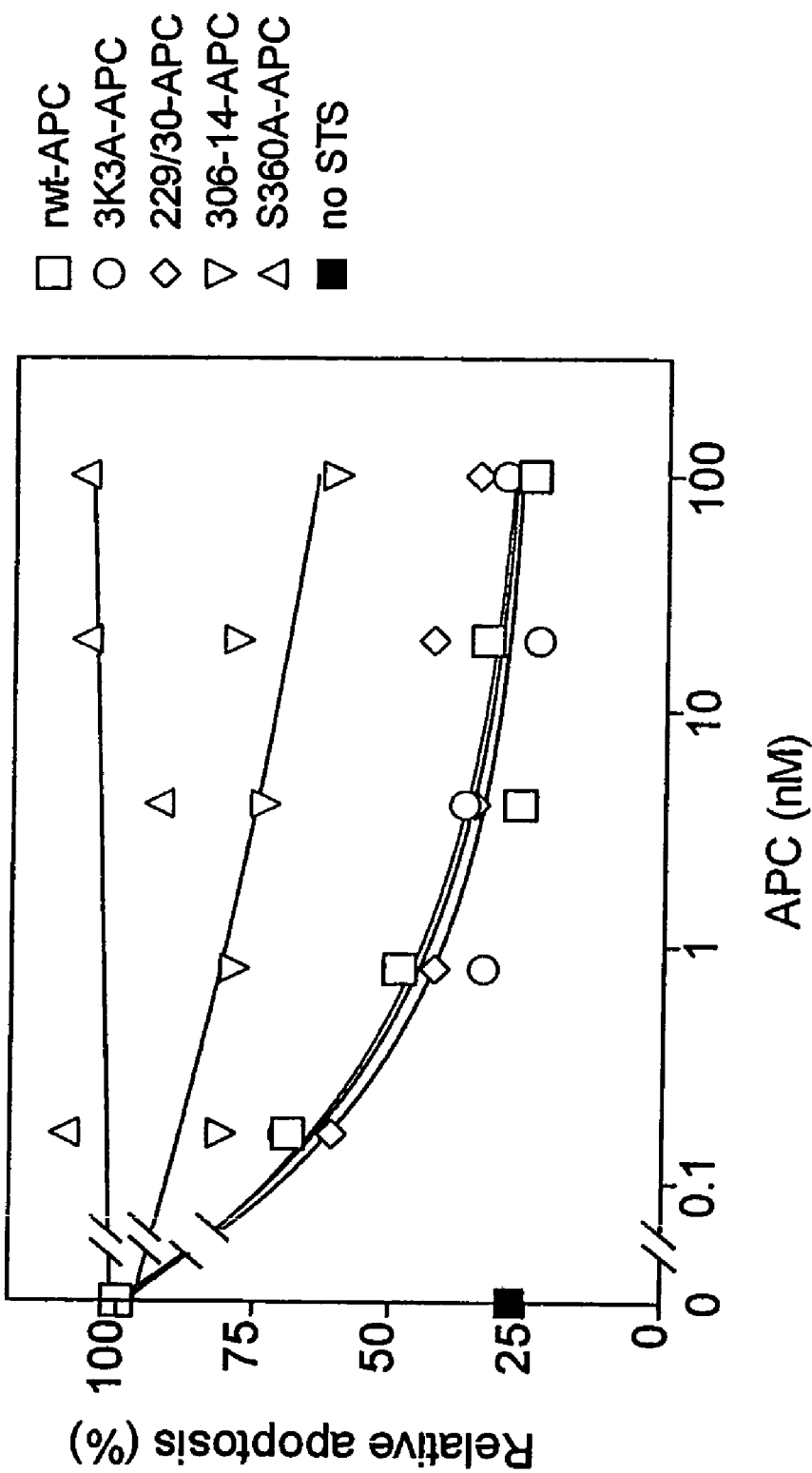

Gale et al. (supra, 2002) have demonstrated that mutations in the surface loops of APC affect its anticoagulant activity.

we constructed a set of APC variants with severely decreased anticoagulant activity but with essentially unchanged enzymatic activity for small peptide (chromogenic) substrates (Gale et al., supra, 2000; Gale et al., supra, 2002). Anticoagulant activity was determined in a dilute prothrombin clotting assay (Gale et al., supra, 2002). The cytoprotective (anti-apoptotic) activity of APC mutants was tested in a staurosporine-induced model of apoptosis with EAhy926 endothelial cells, with the modifications described by Mosnier and Griffin (supra, 2003). It was discovered that APC-mediated inhibition of staurosporine-induced apoptosis required APC's active site, since the inactive APC mutant in which the active site serine360 was replaced by alanine (S360A-APC, see Table 1) (Gale et al., supra, 1997), was devoid of anti-apoptotic activity (Mosnier and Griffin, supra, 2003) (FIGS. 1a and 1b). Recombinant APC inhibition of staurosporine-induced apoptosis in Eahy926 endothelial cells was determined by Apopercentage staining. Inhibition of apoptosis by recombinant wild-type APC (rwt-APC) was dose-dependent (FIG. 1a). Half-maximum inhibition of staurosporine-induced apoptosis was achieved at 0.24 nM rwt-APC, using a 5 hour preincubation of APC with cells before addition of staurosporine. Note the absence of apoptotic activity in the S360A mutant (FIG. 1b). The mutations described in examples 1-3 and their % activities relative to wild-type are indicated in Table 1. Also indicated in Table 1 is the ratio of anti-apoptotic (cytoprotective) activity to anticoagulant activity for each of wild-type APC and mutant APC of examples 1-3, as described in example 4.

TABLE 1

Overview of APC mutants (anticoagulant activity determined by dilute prothrombin time (PT))

| wt mutant | wt-APC sequence (underlined are mutated to alanine) | cyto-protective activity (% wt-APC) | anticoagulant activity (% wt-APC)[1] | Cyto-protective-anticoagulant ratio | FVa inact. Arg$^{506}$ (Arg$^{306}$) (% wt-APC)[1] | Amydolytic activity[1] (% wt-APC) | T½ (min) | SEQ ID |
|---|---|---|---|---|---|---|---|---|
| rwt-APC | n/a | 100% | 100% | 1.0 | 100% (100%) | 100% | 21.4 | |
| 229/230-wt | 225-EYDL<u>RR</u>WEKWE-235 | | | | | | | 2 |
| 229/230-APC | 225-EYDLAAWEKWE-235 | 89% | 6.6% | 13.5 | 25% (110%) | 115% | 27.5 | 3 |
| 3K3A-wt | 189-DS<u>KKK</u>L-194 | | | | | | | 4 |
| 3K3A-APC | 189-DSAAAL-194 | 120% | 15% | 8.0 | 11% (67%) | 134% | 21.0 | 5 |
| 306-314-wt | 305-S<u>R</u>EKEA<u>KRN</u>RT-315 | | | | | | | 6 |
| 306-314-APC | 305-SAEKEAAANAT-315 | <1% | 1.6%[2] | 0.6 | 1.4% (16%) | 75.6% | 46.2 | 7 |

[1]from references (Gale et al., 1997; Gale et al., 2000; Gale et al., 2002); See text and Methods for more information.
[2]determined by APTT instead of dilute PT
n/a: not applicable;
rwt-APC, recombinant wild-type-APC; 229/230-APC, RR229/230AA-APC; 3K3A-APC, KKK191-193AAA-APC; 306-314-APC, R306A/K311A/R312A/R314A-APC.

APC mutants KKK191-193AAA (loop 37), RR229/230AA (calcium loop), RR306/3 12AA (autolysis loop), R306A/K311A/R312A/R314A-APC (autolysis loop) were shown to have 10%, 5%, 17%, and less than 2% of the anticoagulant activity of native APC, respectively. Subsequently, we found that these APC mutants with reduced anticoagulant activity (i.e., KKK191-193AAA, RR229/230AA (Mosnier et al. Blood 104:1740-1744 (2004) and RR306/3 12AA (Mosnier & Griffin, unpublished observations)) retain the anti-apoptotic activity of APC in staurosporine model of apoptosis.

To demonstrate that we could distinguish between structural features of APC necessary for anticoagulant activity versus cell-protective activity, we studied recombinant variant forms of APC that had severely reduced anticoagulant activity. Using double, triple and quadruple combinations of site-directed mutations in the factor Va binding site of APC, Example 1

Replacing the two arginine residues, Arg229 and Arg230, in the calcium-binding loop of APC with alanine residues resulted in a form of APC RR229/230AA-APC (229/230-APC), see Table 1) with only 6.6% residual anticoagulant activity. This reduction in anticoagulant activity of RR229/230AA-APC was primarily due to reduced inactivation of factor Va (FVa) at Arg$^{506}$ whereas cleavage of factor Va at Arg$^{306}$ was much less affected.

The dose-dependence for inhibition of apoptosis by RR229/230AA-APC (FIGS. 1a and 1b) was similar to that of recombinant wild type (rwt)-APC. Half-maximum inhibition of staurosporine-induced apoptosis by RR229/230AA-APC was achieved at 0.27 nM. This example demonstrates that the anticoagulant activity of APC is not required for the cytoprotective (anti-apoptotic) activity of APC.

Example 2

In this example, an APC mutant in which three consecutive lysine residues in loop 37 were replaced with three alanines KKK191-193AAA-APC (3K3A-APC), see Table 1) displayed only 15% residual anticoagulant activity as determined in a dilute prothrombin clotting assay (Gale et al., supra, 2002). The reduction in anticoagulant activity of KKK191-193AAA-APC was due to severely reduced cleavage of factor Va at Arg$^{506}$ (11% of rwt-APC), whereas inactivation of factor Va at Arg$^{306}$ was only moderately affected (67% of rwt-APC) (Table 1). Remarkably, as seen in FIGS. 1a and 1b, the anti-apoptotic activity of KKK191-193AAA-APC was similar to that of rwt-APC with half-maximum inhibition of staurosporine-induced apoptosis at 0.20 nM.

Example 3

In this example, four out of the five basic amino acids in the so-called autolysis loop of APC were replaced by alanine residues, resulting in a form of APC R306A/K311A/R312A/R314A-APC (306-314-APC, see Table 1) having only 1.6% residual anticoagulant activity, as determined by the activated partial thromboplastin time (APTT) [765]. The reduction in anticoagulant activity of R306A/K311A/R312A/R314A-APC was due to severely reduced cleavage of factor Va at Arg506 (1.4% of rwt-APC) whereas inactivation of factor Va at Arg306 was only moderately affected (16% of rwt-APC). The R306A/K311A/R312A/R314A-APC mutant was severely deficient in cytoprotective (anti-apoptotic) activity (FIGS. 1a and 1b), with inhibition of staurosporine-induced apoptosis requiring much higher concentrations of this mutant APC compared to rwt-APC or the other two APC mutants, RR-229/230AA-APC and KKK191-193AAA-APC.

Example 4

Figure 2:
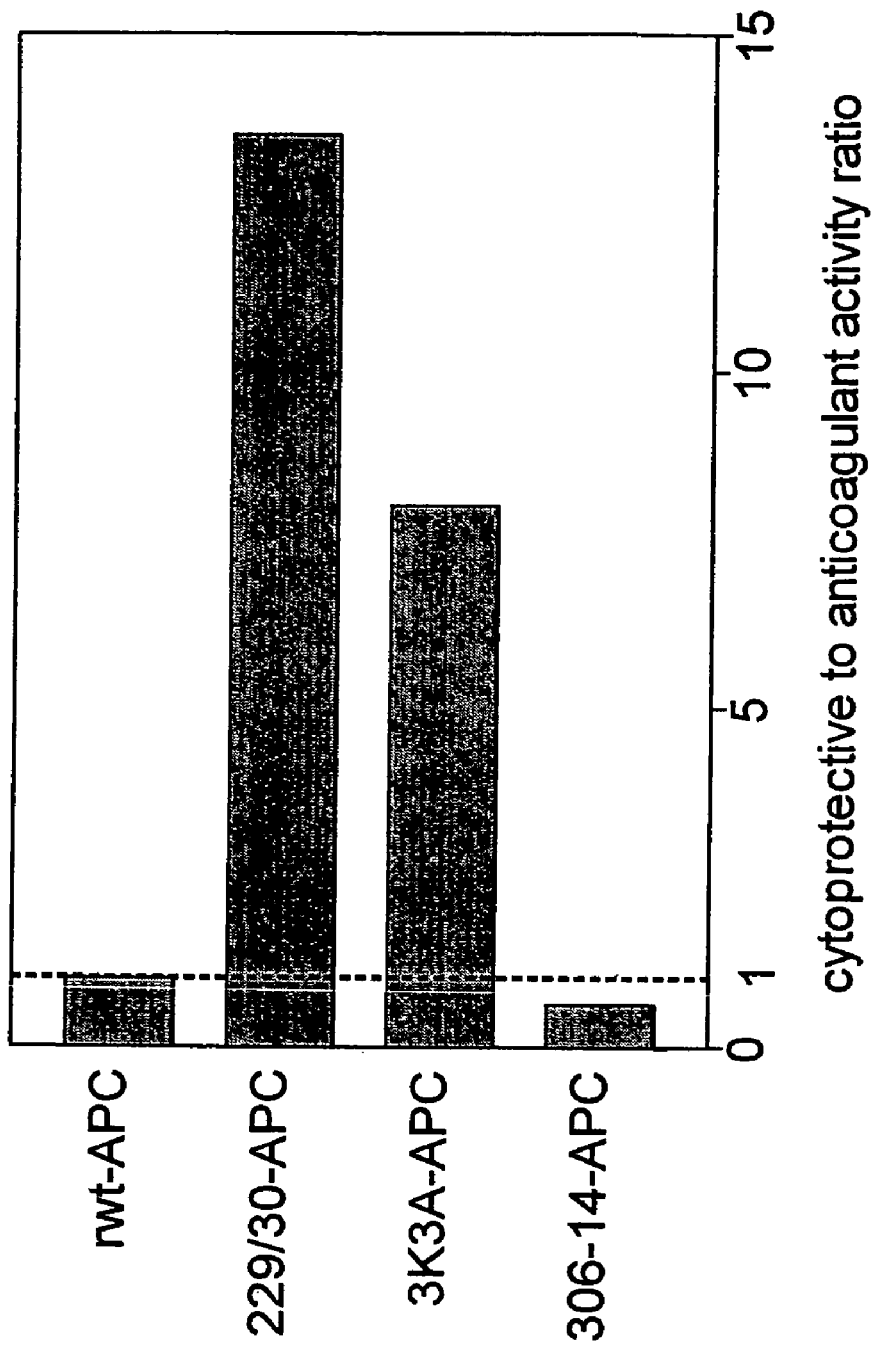
FIG. 2: Ratio of anti-apoptotic (cytoprotective) activity to anticoagulant activity for wild-type and variants of recombinant APC.

The ratio of anti-apoptotic activity to anticoagulant activity was calculated for rwt-APC and for each APC mutant of examples 1-3 (see Table 1), based on the anti-apoptotic activity data in FIG. 1 and published anticoagulant activities (Gale et al., supra, 2000; Gale et al., supra, 2002). The ratio of activities for rwt-APC is defined as 1.0. These ratios, as shown in FIG. 2, indicate that APC mutants with mutations in certain residues in certain protease domain surface loops can exhibit 8-times to 14-times greater anti-apoptotic activity relative to anticoagulant activity. The two mutants, KKK191-193AAA-APC and RR229/230AA-APC, would be expected to exhibit anti-apoptotic or cytoprotective activity comparable to rwt-APC while having an 8-fold to 14-fold reduced risk of bleeding because of the reduction in anticoagulant activity.

The ratio of anti-apoptotic to anticoagulant activity of a recombinant APC mutant may be used to identify variants of recombinant APC of this invention having therapeutic potential. A ratio of >1.0 is indicative of a therapeutic recombinant APC mutant having cytoprotective benefits and reduced risks of bleeding for a subject in need of acute or prophylactic treatment for cell damage, in accordance with this invention. Preferably, a therapeutic variant of recombinant APC would have a ratio of anti-apoptotic activity to anticoagulant activity of greater than about 2. More preferably, said ratio would be greater than about 4. Most preferably, said ratio would be greater than about 8.

Prodrug embodiments of this invention may involve recombinant protein C variants that, following conversion of protein C to APC either in vitro or in vivo, exhibit reduced anticoagulant activity while retaining normal or near-normal cell protective activities, i.e., have a ratio of anti-apoptotic: anticoagulant activity greater than 1.0. Preferably, the prodrugs of the invention may be converted to APC variants that have a ratio of anti-apoptotic activity to anticoagulant activity that is greater than about 2, more preferably the ratio is greater than about 4 or most preferably the ratio is greater than about 8.

The invention comprises several embodiments which are described below.

In one embodiment, the variants of APC of the invention may be used in effective doses to provide cytoprotection to cells at risk for undergoing apoptotic cell death or stress-induced injury either in vivo or in vitro. In an aspect of this embodiment the APC variants may be administered in therapeutic doses to subjects who could benefit from APC's cytoprotective activities that are independent of the anticoagulant activity. Such subjects comprise patients at risk for damage to blood vessels or other tissue organs, which damage is caused at least in part by apoptosis. The risk for cell damage may be the result of any one or more of sepsis, ischemia/reperfusion injury, stroke, ischemic stroke, acute myocardial infarction, acute neurodegenerative disease, chronic neurodegenerative disease, organ transplantation, chemotherapy, or brain radiation injury. These causes of cell damage are not intended in any way to limit the scope of the invention, as one skilled in the art would understand that other diseases or injuries also may put cells at risk for damage caused at least in part by apoptosis. The effective doses or therapeutic doses will be those that are found to be effective at preventing or alleviating cell damage caused at least in part by apoptosis. In another aspect of this embodiment, the variants of the invention may be applied to cells or tissue in vitro or in situ in vivo.

In another embodiment, the variants of APC or prodrugs of the invention may be used to formulate pharmaceutical compositions with one or more of the utilities disclosed herein. The therapeutic compositions may be administered in vitro to cells in culture, in vivo to cells in the body, or ex vivo to cells outside of a subject, which may then be returned to the body of the same subject or another. The cells may be removed from, transplanted into, or be present in the subject (e.g., genetic modification of endothelial cells in vitro and then returning those cells to brain endothelium). The prodrugs would be expected to be capable of being converted to APC in situ. Candidate agents may also be screened in vitro or in vivo to select those with desirable properties. The cell may be from the endothelium (e.g., an endothelial or smooth muscle cell or from the endothelium of a brain vessel).

Therapeutic compositions comprising the variant APC of the invention may be provided in dosage form. In one aspect of this embodiment, the therapeutic compositions of the invention may further comprise a pharmaceutically acceptable carrier and may still further comprise components useful for delivering the composition to a subject's brain. Such pharmaceutical carriers and delivery components are known in the art. Addition of such carriers and other components to the composition of the invention is well within the level of skill in this art. For example, a permeable material may release its contents to the local area or a tube may direct the contents of a reservoir to a distant location of the brain.

The pharmaceutical compositions of the invention may be administered as a formulation, which is adapted for direct application to the central nervous system, or suitable for passage through the gut or blood circulation. Alternatively, pharmaceutical compositions may be added to the culture medium. In addition to active compound, such compositions may contain pharmaceutically-acceptable carriers and other ingredients known to facilitate administration and/or enhance uptake. It may be administered in a single dose or in multiple doses, which are administered at different times. A unit dose of the composition is an amount of APC mutants provides cytoprotection, inhibits apoptosis or cell death, and/or promotes cell survival but does not provide a clinically significant anticoagulant effect, a therapeutic level of such activity, or has at least reduced anticoagulant activity in comparison to previously described doses of activated protein C. Measurement of such values are within the skill in the art: clinical laboratories routinely determine these values with standard assays and hematologists classify them as normal or abnormal depending on the situation. Examples of how to measure such values are described below.

The pharmaceutical compositions of the invention may be administered by any known route. By way of example, the composition may be administered by a mucosal, pulmonary, topical, or other localized or systemic route (e.g., enteral and parenteral). In particular, achieving an effective amount of activated protein C, prodrug, or functional variant in the central nervous system may be desired. This may involve a depot injection into or surgical implant within the brain. "Parenteral" includes subcutaneous, intradermal, intramuscular, intravenous, intra-arterial, intrathecal, and other injection or infusion techniques, without limitation.

Suitable choices in amounts and timing of doses, formulation, and routes of administration can be made with the goals of achieving a favorable response in the subject (i.e., efficacy or therapeutic), and avoiding undue toxicity or other harm thereto (i.e., safety). Administration may be by bolus or by continuous infusion. Bolus refers to administration of a drug (e.g., by injection) in a defined quantity (called a bolus) over a period of time. Continuous infusion refers to continuing substantially uninterrupted the introduction of a solution into a blood vessel for a specified period of time. A bolus of the formulation administered only once to a subject is a convenient dosing schedule, although in, the case of achieving an effective concentration of activated protein C in the brain more frequent administration may be required. Treatment may involve a continuous infusion (e.g., for 3 hr after stroke) or a slow infusion (e.g., for 24 hr to 72 hr when given within 6 hr of stroke). Alternatively, it may be administered every other day, once a week, or once a month. Dosage levels of active ingredients in a pharmaceutical composition can also be varied so as to achieve a transient or sustained concentration of the compound or derivative thereof in a subject and to result in the desired therapeutic response.

Thus, "therapeutic" refers to such choices that involve routine manipulation of conditions to achieve a desired effect (e.g., inhibition of apoptosis or cell death, promotion of cell survival, cytoprotection, neuroprotection, or combinations thereof). The amount of mutant protein C or mutant activated protein C administered to subjects may be higher than doses of recombinant protein C or activated protein C, if necessary for maximal cytoprotection, because of the reduced risk of bleeding. In this manner, "therapeutic amount" refers to the total amount of activated protein C variant or protein C variant that achieves the desired cytoprotective effect, but with reduced risk for bleeding due to reduced anticoagulant activity (for bolus administration, e.g., 2 mg/kg or less, 1 mg/kg or less, 0.5 mg/kg or less, 0.04 mg/kg or less, 0.03 mg/kg or less, 0.02 mg/kg or less, 0.01 mg/kg or less, 0.005 mg/kg or less, depending on the species of the subject or disease to be treated).

The therapeutic amount may be about 0.01 mg/kg/hr to about 1.1 mg/kg/hr, for example, administered by continuous infusion over 4 hour to 96 hour, to as little as about 0.01 mg/kg/hr to about 0.10 mg/kg/hr for about 24 hours. Preferably, the therapeutic dose would be administered by continuous infusion for about 4 to about 72 hours. More preferably, by continuous infusion for about 4 to about 48 hours. More preferably, by continuous infusion for about 12 to about 48 hours. More preferably, by continuous infusion for about 12 to about 36 hours. More preferably, by continuous infusion for about 4 to about 36 hours. More preferably, by continuous infusion for about 12 to about 24 hours. Most preferably, by continuous infusion for about 24.

The therapeutic amount may be based on titering to a blood level amount of APC of about 0.01 μg/ml to about 1.6 μg/ml, preferably from about 0.01 μg/ml to about 0.5 μg/ml. It is also within the skill of the art to start doses at levels lower than required to achieve the desired therapeutic effect and to gradually increase the dosage until the desired effect is achieved. It is likewise within the skill of the art to determine optimal concentrations of variants to achieve the desired effects in the in vitro and ex vivo preparations of the invention, e.g., about 1-100 nM.

In yet another embodiment, a method of screening candidate agents to identify other variants of recombinant APC having therapeutic potential in accordance with the invention is provided. One aspect of this embodiment comprises mutating the recombinant APC or protein C at any surface loop of the protease domain and determining the variant APC's anticoagulant and cytoprotective activities in assays as described. The method of the embodiment further comprises measuring the anticoagulant activity of said mutated recombinant activated protein C; measuring the anti-apoptotic activity of said mutated recombinant activated protein C; calculating the ratio of anti-apoptotic activity to anticoagulant activity; identifying the recombinant activated protein C as potentially therapeutic if said ratio is greater than 1.0. Preferably, the ratio is greater than about 2, more preferably the ratio is greater than about 4, most preferably the ratio is greater than about 8. Where the candidate agent is a prodrug, the prodrug may comprise a protein C variant, which is capable of being converted to an activated protein C variant either in vivo or in vitro. To screen the candidate protein C variant for desirable properties in accordance with the invention, the protein C variant would be converted to the activated form (APC) prior to measuring activities.

In another aspect of this embodiment, a library of candidate agents is selected which are variants of recombinant APC or protein C having at least one mutation at a residue in a protease domain of a surface loop selected from the group consisting of loop 37, calcium loop, and autolysis loop. The method comprises converting the protein C variant to activated protein C variant; determining anti-apoptotic activity of said candidate agents in one or more stressed or injured cells by exposing said cells to an apoptotic-inducing concentration of staurosporine in the presence of an amount of a candidate agent; determining anticoagulant activity of said candidate agents in one or more stressed or injured cells exposing cells to same amount of the same candidate agent as in (b), and performing a dilute prothrombin time clotting assay; calculating the ratio of the anti-apoptotic activity determined in (a) to the anticoagulant activity of (b); and selecting candidate agents having an anti-apoptotic:anticoagulant activity ratio greater than 1.0. Preferably, the ratio is greater than about 2, more preferably the ratio is greater than about 4, most preferably the ratio is greater than about 8.

Other permutations of this basic scheme of screening for candidate agents are within the ordinary skill in the art and are encompassed by the invention. Examples of such permutations non-exclusively include using other methods of inducing apoptosis and other tests for measuring apoptotic activity and anticoagulant activity.

Methods

Protein C Activation

Recombinant forms of protein C can be produced with a selected chemical structure (e.g., native, mutant, or polymorphic). As an illustration, a gene encoding human protein C is described in U.S. Pat. No. 4,775,624 and can be used to produce recombinant human protein C as described in U.S. Pat. No. 4,981,952. Human protein C can be recombinantly produced in tissue culture and activated as described in U.S. Pat. No. 6,037,322. Natural human protein C can be purified from plasma, activated, and assayed as described in U.S. Pat. No. 5,084,274. The nucleotide and amino acid sequence disclosed in these patents may be used as a reference for protein C.

In the above examples of this invention, recombinant wild-type APC (wt- APC), RR229/230 AA-APC (229/230 -APC), KKK191/192/193 AAA-APC (3K3 A-APC), R306A/K311A/R312A/R314A-APC (306-314-APC) and S360A-APC were prepared as described (Gale et al., supra, 1997; Gale et al., supra, 2000; Gale et al., supra, 2002). Protein C was activated by thrombin (3281 U/mg, Enzyme Research Labs, South Bend, IN). Protein C in HBS (HEPES buffered saline, 50 mM HEPES, 150 mM NaCl) with 2 mM EDTA and 0.50o bovine serum albumin (nSA), pH 7.4, at a concentration of 600 ⊥/mL was incubated for 2.5 hours with 12 ⊥/mL thrombin at 37° C., followed by the addition of 1.1 units of hirudin (Sigma, St Louis, MO) per unit of thrombin to inactivate the thrombin. Controls were done in amidolytic assays, APTT clotting assays and FVa inactivation assays to verify that the thrombin and hirudin used had no effect on subsequent assays.

A "mutation" refers to one or more changes in the sequence of polynucleotides and polypeptides as compared to native activated protein C, and has at least one function that is more active or less active, an existing function that is changed or absent, a novel function that is not naturally present, or combinations thereof.

Active-Site Titration of APC

All APC mutants were quantitated using an active site titration adapted from Chase and Shaw (Biochem. Biophys. Res. Commun., 29:508-514, 1967) using APC at approximately 8 µM in HBS and p-nitrophenol-guanidino benzoate at 0.1 mM with an extinction coefficient for p-nitrophenol of 11400 $M^{-1}$ $cm^{-1}$ calculated for pH 7.4.

Kinetic Analysis of APC

Michaelis constants ($K_m$) and catalytic rate constants ($k_{cat}$) for the chromogenic substrate, Pefachrome PCa (Pentapharm, Basel, Switzerland), were determined by varying substrate concentration from 1.43 mM to 0.0446 mM in HBS, 0.5% BSA, 5 mM $CaCl_2$, pH 7.4 with APC at 5.7 nM. Michaelis constants were derived using Eadie-Hofstee plots. Alternatively, the 5 mM $CaCl_2$ was replaced with 5 mM EDTA for similar determinations. Color development was measured with an Optimax microplate reader (Molecular Devices, Sunnyvale, Calif.) (Mesters et al., J. Biol. Chem., 266:24514-19, 1991).

Cell Culture

EAhy926 endothelial cells were obtained from Dr. C. J. S. Edgell (University of North Carolina, Chapel Hill N.C.) and were maintained in DMEM high glucose (Gibco, Grand Island, N.Y.) with 10% fetal bovine serum (Omega Scientific, Tarzana, Calif.), 100 U/ml penicillin G sodium (Gibco), 100 µg/ml streptomycin sulphate (Gibco) and 2 mM glutamine (Gibco) at 37° C. in a humid atmosphere containing 5% $CO_2$ in air as described (Edgell et al., Proc. Nat'l Acad. Sci., USA, 80:3734-3737, 1983).

Apoptosis Assay

Staurosporine-induced apoptosis of endothelial cells was initiated using our modifications (Mosnier and Griffin, supra, 2003) of the previously described assay (Joyce et al., supra, 2001). The modifications involved culturing the cells on gelatin-coated coverslips, changing the staurosporine concentration and optimizing the APC preincubation times before addition of staurosporine as described below. Staurosporine, an ATP analogue and inhibitor of protein kinase C (PKC), is a well known and potent inducer of apoptosis. Apopercentage dye is a measurement of expression of phosphatidylserine on the outside surface of the cell membrane and is therefore similar to what is measured by traditional annexin-V labeling. The transfer of phosphatidylserine to the outside surface of the cell membrane permits the unidirectional transport of the Apopercentage dye inside the cell where it is retained and accumulates. The accumulated dye has a red/purple color and is visible under a conventional microscope (Joyce et al., supra, 2001; Mosnier and Griffin, supra, 2003). We used this dye to monitor apoptosis. Alternatively, cells may be incubated with the apoptosis specific dye, YO-PRO-1 (10 µM, 5 min) (Molecular Probes, Eugene, Oreg.) as described (Idziorek et al., J. Immunol. Methods, 185:249-258,1995) or for 20 min with the synthetic substrate for caspase 3-like enzymes, DEVD-amc (Calbiochem, San Diego, Calif.). Staurosporine induced a time-dependent and concentration-dependent apoptosis in EAhy926 endothelial cells, as determined by Apopercentage staining (data not shown).

Briefly, 12 mm round coverslips (Fisherbrand, Pittsburgh, Pa.) were acid washed, rinsed with distilled water and 95% ethanol, dipped 10× in gelatin (0.5% gelatin provided with the Apopercentage dye) until an homogenous drop was formed and air dried. EAhy926 cells were grown to confluency on gelatin-coated coverslips in 24 well plates and incubated with APC for 5 hours prior to apoptosis induction. After the preincubation with the various proteins, apoptosis was induced by addition of staurosporine (Calbiochem, San Diego, Calif.) to a final concentration of 10 µM in the presence of the Apopercentage dye (Biocolor, Belfast, N. Ireland) diluted to a final concentration of 1/20 of the provided stock solution per the manufacturer's instructions.

After 1 hour incubation at 37° C. in a humid atmosphere containing 5% $CO_2$ in air the cells were washed in phosphate buffered saline (PBS) and 500 µl of DMEM high glucose without phenol red (Gibco, Grand Island, N.Y.) with 5% fetal bovine serum (Omega Scientific, Tarzana, Calif.), 100 U/ml penicillin G sodium (Gibco), 100 mg/ml streptomycin sulphate (Gibco) and 2 mM glutamine (Gibco) added to the cells.

Cells were photographed immediately after washing, using a Zeiss IM inverted microscope connected to a Spot QE digital camera. An average of 4 fields at 100× magnification were photographed per coverslip and numbers of apoptotic cells were counted using the image analysis software Cell Counter (written by Dr. L. O. Mosnier, The Scripps Research Institute). For each experiment representative fields of the cells were photographed using phase contrast and the total number of cells present was counted. The percentage of apoptosis is expressed as the number of apoptotic cells relative to the total number of cells. Repeated control experiments were performed (MTT based assay, Celltiter 96 Aqueous non-radioactive cell proliferation assay, Promega, Madison, Wis.) to ascertain that the cells did not become detached. In addition, on occasions when disruption of the confluent cell layer was observed, the data point was excluded from further analysis and repeated.

Clotting Assays

Dilute prothrombin time clotting assays were performed, as follows. Plasma (50 μL) was incubated with 50 μL of APC in HBS with 0.5 % BSA at APC concentrations from 8 to 32 nM (2.7-11 nM final concentration) for 3 min at 37° C. Then clotting was initiated by adding 50 μL Innovin (Dade Behring Inc., Newark, Del.) diluted 1:60 in HBS, 0.5% BSA, 25 mM $CaCl_2$. The clotting time was measured using an ST4 coagulometer (Diagnostica Stago, Asnieres, France). For APTT clotting assays, 50 μL of plasma was mixed with 50 μL of APTT reagent (Platelin LS, Organon Technika Corp, Durham, N.C.) and preincubated for at 37° C. for 3 minutes. Then 2 μL APC was added followed by 50 μL of HBS, 0.5% BSA, 5 mM $CaCl_2$. The clotting time was recorded using an ST4 coagulometer (Diagnostica Stago, Asnieres, France).

APC Inactivation

APC inactivation by serpins present in plasma was measured essentially according to the protocol of Heeb et al (J. Biol. Chem., 265:2365-2369, 1990). Briefly, either human plasma or a mix of pure serpin inhibitors (PCI and/or α1-antitrypsin) was preincubated at 37° C., then APC was added. At selected times aliquots were removed and assayed for APC activity with an APC specific chromogenic substrate.

Factor Va Inactivation

Inactivation of FVa was measured as follows. A mixture of 1 nM FVa with 25 μM phospholipid vesicles was made in 50 mM HEPES, pH 7.4, 100 mM NaCl, 0.5% BSA, 5 mM $CaCl_2$, 0.1 mM $MnCl_2$. Inactivation was initiated by the addition of APC. One microliter aliquots were removed at time points and added to 40 μL containing 1.25 nM factor Xa (FXa) with 31 μM phospholipid vesicles, followed by addition of 10 μL 3 μM prothrombin (final concentrations: 1 nM FXa, 20 PM FVa, 25 μM phospholipid vesicles and 0.6 μM prothrombin). After 2.5 min a 15 μL aliquot of this mixture was quenched by addition to 55 μL HBS containing 10 mM EDTA, 0.5% BSA, pH 8.2. Chromogenic substrate CBS 34-47 (Diagnostica Stago, Asnieres, France) was added and the rate of thrombin formation was assessed by measuring the change in absorbance at 405 nm. Curve fitting of these pseudo-first order time courses of FVa inactivation was done according to Nicolaes et al. (supra, 1995) using equation 1:

$$Va_t = Va_0 \cdot e^{-(k_{506}+k'_{306})\cdot t} + B \cdot Va_0 \cdot \frac{k_{506} \cdot e^{(-k_{306} \cdot t)}}{(k_{506}+k'_{306}-k_{306})} \cdot \left(1 - e^{-(k_{506}+k'_{306}-k_{306})\cdot t}\right) \quad \text{equation 1}$$

Those skilled in the art will recognize other disease states and/or symptoms, which might be treated and/or mitigated by the present invention. For example, the present invention may be used to treat myocardial infarction, other heart diseases and their clinical symptoms, endothelial injury, adult respiratory distress syndrome (ARDS), and failure of the liver, kidney, or central nervous system (CNS). There are many other diseases which benefit from the methodologies of the present invention such as for example, coronary arterial occlusion, cardiac arrhythmias, congestive heart failure, cardiomyopathy, bronchitis, neurotrauma, graft/transplant rejection, myocarditis, diabetic neuropathy, and stroke. Life threatening local and remote tissue damage occurs during surgery, trauma, and stroke when major vascular beds are deprived for a time of oxygenation (ischemia) then restored with normal circulation (reperfusion). Cell death and tissue damage can lead to organ failure or decreased organ function. The compositions and methodologies of the present invention are useful in treatment of such injury or prevention thereof.

In summary, two examples of the variants of recombinant APC mutants of this invention, namely KKK191-193AAA-APC and RR229/230AA-APC are provided, that have substantial reductions in anticoagulant activity but that retain normal or near-normal levels of anti-apoptotic activity. The invention encompasses APC variants such as these, which have the highly desirable property of a high ratio of anti-apoptotic to anticoagulant activity. The invention further encompasses variants having more modest, yet still beneficial, ratios of anti-apoptotic to anticoagulant activity; such variants also would be expected to be cytoprotective while having significantly reduced risk of bleeding. The invention is not limited to variants of APC, but also includes protein C mutants which are capable of yielding desirable APC mutants, i.e., those that would have the same desirable activity ratios. The invention also is not limited to mutations on loop 37, calcium loop, or autolysis loop; the invention encompasses mutations of residues on other surface loops of the protease domain that produce the desired cytoprotective to anticoagulant ratio. Thus, APC and protein C variants of the invention are expected to be useful for therapy for subjects who will benefit from APC protective activities that are independent of APC's anticoagulant activity. Subjects would include patients at risk of damage from apoptosis to blood vessels or tissue in various organs. More specifically, but not exclusively, these subjects will include, for example, those suffering severe sepsis, ischemia/reperfusion injury, ischemic stroke, acute myocardial infarction, acute or chronic neurodegenerative diseases and organ transplantation, among other conditions.

Example 5

Methods

This example includes refined data from Table 1 incorporating additional experiments that are averaged in and improved data analysis along with data for the variant S360A-APC. Furthermore, the anticoagulant data was collected using the APTT assay instead of the PT assay (as mentioned in Table 2). Therefore, this refined data is presented as Table 2. This example also includes more detailed analysis of the amidolytic, anticoagulant and anti-apoptotic activities of the variants of APC (FIGS. 3-6). For this example, the following methods were employed.

Human alpha-thrombin was purchased from Enzyme Research Laboratories (South Bend, Ind.). Normal human citrate-anticoagulated plasma was from George King Bio-Medical, Inc. (Overland Park, Kans.). The chromogenic substrate L-Pyroglutamyl-L-prolyl-L-arginine-p-Nitroaniline hydrochoride (S-2366) was obtained from Chromogenix (Franklin, Ohio).

Preparation of Recombinant Activated Protein C

Mutant protein C expression vectors were constructed and recombinant protein C mutants were purified from conditioned media as described (Gale et al., supra, 2002; Gale et al., supra, 1997). Purified protein C was activated by thrombin (Gale et al., supra, 2002; Gale et al., supra, 1997). Briefly, Protein C in HBS (50 mM HEPES, 150 mM NaCl) with 2 mM EDTA and 0.5% BSA, pH 7.4, at a concentration of 600 μg/ml was incubated for 2.5 h with 12 μg/ml thrombin at 37° C. followed by the addition of 1.1 units of hirudin per unit of thrombin to inactivate the thrombin. Subsequently, thrombin was removed by anion-exchange chromatography with NaCl gradient elution (Yan et al., Biotechnology, 8:655-661, 1990). Residual thrombin, as determined by fibrin clotting, accounted for less than 0.00025% (mol thrombin/mol APC) of the protein. Concentrations of rwt-APC and APC mutants were determined by active-site titration adapted from Chase and Shaw (Chase and Shaw, supra, 1967) using APC at ~8 μM in HBS and p-nitrophenol-guanidino benzoate at 0.1 mM and using an extinction coefficient for p-nitrophenol of 11,400 $M^{-1}cm^{-1}$ (at pH 7.4) as described (Gale et al., supra, 2002). The concentration of S360A-APC was determined by Asserachrom Protein C ELISA from American Bioproducts (Parsippany, N.J.) (Gale et al., supra, 1997).

APC Activity Assays

Amidolytic (S-2366) assays were performed as described (Gale et al., supra, 2000; Gale et al., supra, 1997). APTT clotting time assays were performed according to the following procedure. Plasma (50 μl) was incubated for 1 min with kaolin/cephalin (50 μl) (C.K. Prest 2, Diagnostica Stago, Parsippany, N.J.) at 37° C., and then 25 μl APC in HBS with 0.5% BSA was added at final APC concentrations from 0.5 nM-32 nM and incubated for an additional 3 min. Clotting was then initiated by adding 50 μl of 50 mM $CaCl_2$ in HBS and the clotting time was recorded using an Amelung KC 4a micro coagulometer (Sigma Diagnostics, St Louis, Mo.).

APC's cytoprotective effects were determined in assays of staurosporine-induced endothelial cell (EA.hy926) apoptosis as described (Mosnier and Griffin, supra, 2003). APC (0.16-100 nM) was incubated with cells for 5 h prior to induction of apoptosis by staurosporine (10 μM, 1 h) unless otherwise indicated, and apoptosis was assessed by Apopercentage dye from Biocolor (Belfast, N. Ireland) which measures phosphatidylserine translocation to the outside surface of the cell membrane. Blocking antibodies against PAR-1 (WEDE-15 and ATAP-2 kindly provided by Dr L. Brass) and against EPCR (Zymed) were used as described (Mosnier and Griffin, supra, 2003). For activated caspase-3 immunofluorescence staining and DAPI nuclear staining (5 μg/ml) of staurosporine-treated (2 μM, 4 h) EA.hy926 endothelial cells that had been incubated with APC (25 nM, 5 h) prior to apoptosis induction, the manufacturer's instructions were followed using a rabbit anti-activated caspase-3 antibody (Promega) and Alexa-fluor-568 labeled secondary goat anti-rabbit (Molecular Probes).

PAR-1 Peptide Cleavage.

The interactions of rwt-APC and APC variants (500 nM) with PAR-1 N-terminal tail peptide (TR33-62) were studied using a synthetic peptide representing PAR-i residues 33-62 (Bio Synthesis Inc., Lewisville, TX). The peptide sequence was $A^{33}TNATLDPR^{41}SFLLRNPNDKYEPFWEDEEKN^{62}$ (SLO ID. 8) and was cleaved by APC between Arg41 and Ser42. The substrate peptide and the two peptide products of thrombin or APC cleavage at Arg41 (TR33-41 and TR42-62) were resolved and analysed by reverse phase HPLC and quantified essentially as described (Arosio et al., Biochemistry, 39:8095-8101, 2000). All TR33-62 cleavage experiments with APC contained 5 nM hirudin to assure that the observed cleavage was not due to thrombin contamination.

Results

The anti-apoptotic, anticoagulant and amidolytic activities of RR229/230AA-APC and KKK191-193-AAA-APC were determined and compared to the activities of recombinant wild type (rwt)-APC and of a hydrolytically inactive mutant, S360A-APC, containing Ala in place of the active site residue, Ser360. The two APC protease domain loop variants, RR229/230AA-APC and KKK191-193-AAA-APC, had the same enzymatic activity against a small chromogenic substrate, S-2366, as recombinant wild-type APC (rwt-APC) (FIG. 3a), indicating the structural and functional preservation of the APC active site, whereas these variants had markedly decreased anticoagulant activity (FIG. 3b) that was due to impaired cleavage at Arg506 in factor Va (see Table 2).

TABLE 2

Recombinant wild type and mutant APC activities.*
(anticoagulant activity determined by APTT)

| wt Mutant | APC sequence (mutated to Ala) | cytoprotective activity (% rwt-APC)† | anticoagulant activity (% rwt-APC)‡ | cytoprotective to anticoagulant ratio$ | factor Va inactivation cleavage at $Arg^{506}$ ($Arg^{306}$) (% rwt-APC)‖ | amidolytic activity (% rwt-APC)¶ | PAR-1 peptide (TR33-62) cleavage (% rwt-APC)# | SEQ ID |
|---|---|---|---|---|---|---|---|---|
| rwt-APC* | none | 100% | 100% | 1.0 | 100% (100%) | 100% | 100% | |
| 229/230-wt | 227-DLRRWE-232 | | | | | | | 9 |
| 229/230-APC | 227-DLAAWE-232 | 94% | 13% | 7.2 | 25% (110%) | 102% | 116% | 10 |
| 3K3A-wt | 189-DSKKKLA-195 | | | | | | | 11 |
| 3K3A-APC | 189-DSAAALA-195 | 114% | 4.6% | 25 | 11% (67%) | 109% | 88% | 12 |
| S360A-wt | 358-GDSGG-362 | | | | | | | 13 |
| S360A-APC | 358-GDAGG-362 | <1%** | 23%†† | 0 | <1%** (<1%**) | <1%** | <3%** | 14 |

*Recombinant wild-type APC (rwt-APC) activity was defined as 100% and values for mutant APC's are given as percentage of rwt-APC activity.
†Derived from the concentrations of APC required for half-maximal inhibition of the staurosporine-induced apoptosis (FIG. 2a).
‡Based on the APTT dose-response data determined for rwt-APC and APC variants (0.5 nM-32 nM) (FIG. 1b). Mosnier et al. Blood 104:1740-1744 (2004).
$Derived from the ratio of relative activities for cytoprotective and anticoagulant activities given in the previous two columns of this Table.
‖Based on apparent second-order rate constants determined previously (Gale et al., supra, 2002; Gale et al., supra, 1997).
¶Based on the amidolytic activity determined for rwt-APC and APC variants (0.5 nM-32 nM) (FIG. 1a). Mosnier et al. Blood 104:1740-1744 (2004).
Based on the catalytic efficiency derived from FIG. 4 for cleavage of the PAR-1 peptide (TR33-62) by rwt-APC and APC variants (500 nM).
**No detectable activity under the conditions of the assay.
††Anticoagulant activity of S360A-APC is not due to proteolysis of factor Va and in contrast to rwt-APC is independent of the incubation time of APC with the plasma (Gale et al., supra, 1997).

Figure 3A:
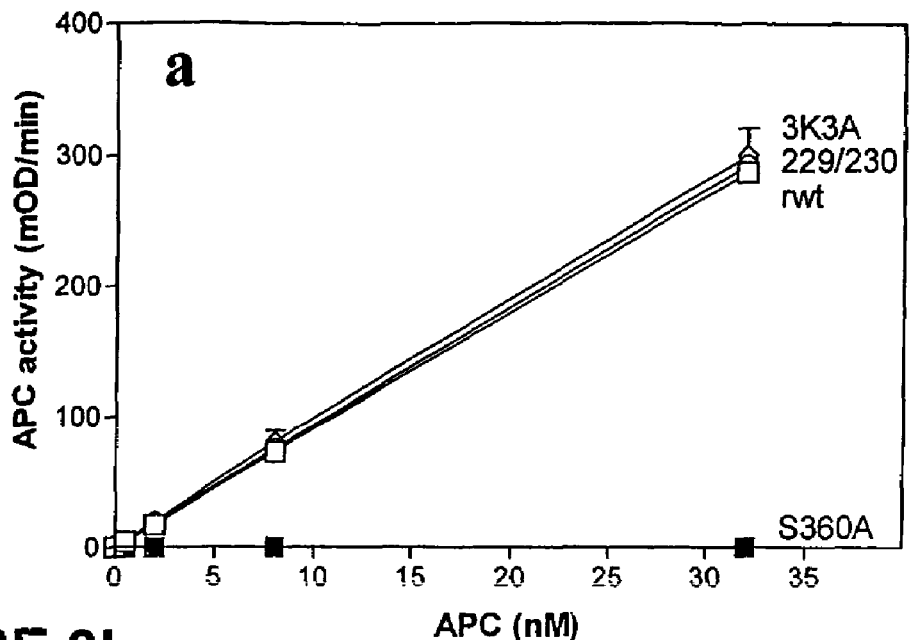
FIG. 3a-3b: Amidolytic and anticoagulant activity of rwt-APC and APC variants. a, Amidolytic activity of rwt-APC and APC variants against the small chromogenic substrate, S-2366. b, Anticoagulant activity of rwt-APC and APC variants determined using Activated Partial Thromboplastin Time (APTT) assays. Each point represents the mean±S.E.M. from at least three independent experiments. Symbols denote: □, rwt-APC; ○, RR229/230AA-APC; ◇, KKK191-193AAA-APC; ■, S360A-APC.
Figure 3B:
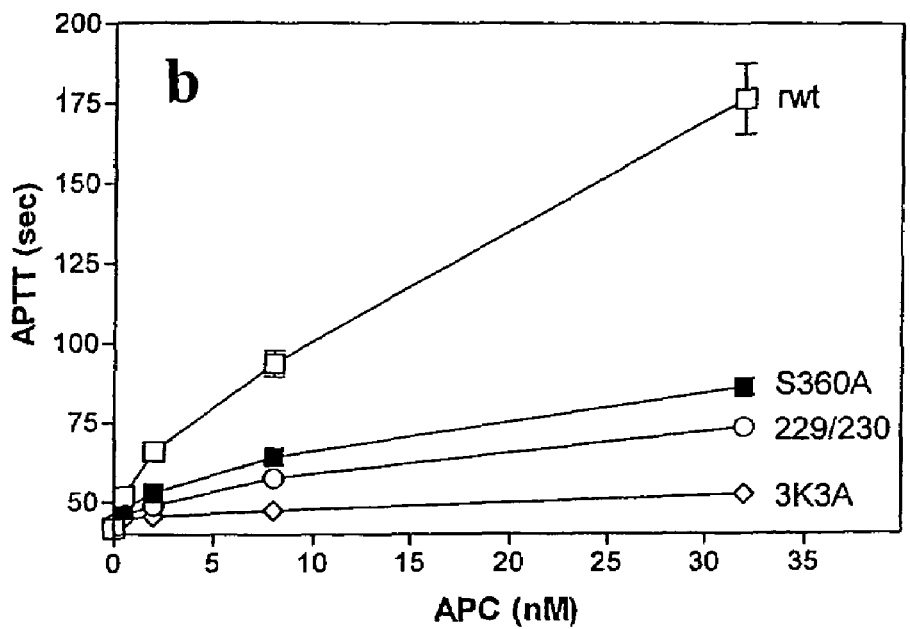

Although S360A-APC had no chromogenic activity (FIG. 3a), the anticoagulant activity of S360A-APC was ~23% in the conditions of the APTT assay (FIG. 3b). As previously described, in contrast to normal rwt-APC, this anticoagulant activity is independent of the incubation time of APC with plasma (Gale et al., supra, 1997) and appears to involve binding of APC exosites to factor Va such that there is inhibition of factor Xa and prothrombin binding to factor Va.

Figure 4A:
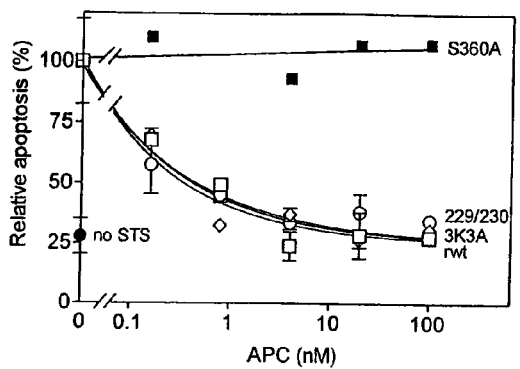
FIG. 4a-4c: Anti-apoptotic activity of rwt-APC and anticoagulantly impaired APC variants. a, Inhibition of staurosporine (STS)-induced apoptosis by APC (see Methods). Percentage of apoptotic endothelial cells observed in the absence of added APC (18% of all cells) was taken as 100%. Each point represents the mean±S.E.M. from at least three independent experiments. Symbols used denote: □, rwt-APC; ○, RR229/230AA-APC; ◇, KKK191-193AAA-APC; ■, S360A-APC; •, no staurosporine. b, c, Reduction of activated caspase-3-positive cells by rwt-APC and APC variants (25 nM, 5 h) upon induction of apoptosis by staurosporine (2 μM, 4 h). b, Activated caspase-3-positive cells expressed as a percentage of the total number of cells present. As indicated by the "no STS", thin line, approximately 2% of the endothelial cells were positive for activated caspase-3 in the absence of staurosporine. Each bar represents the mean±SEM of two to four independent experiments. c, Immunofluorescence analysis of activated caspase-3-positive cells using an activated caspase-3 specific antibody (red) and DAPI nuclear staining (blue). Columns represent identical fields. Original magnification was 200×.
Figure 4B:
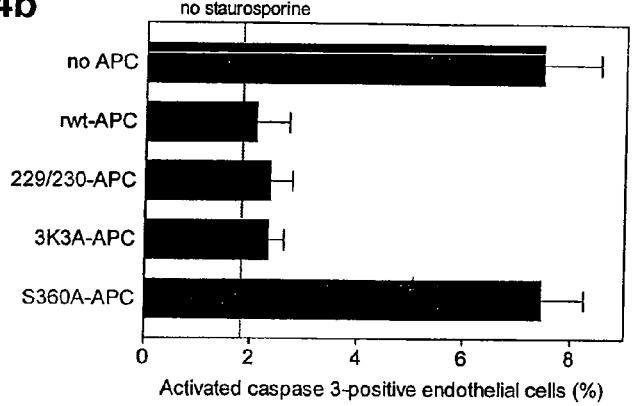
Figure 4C:
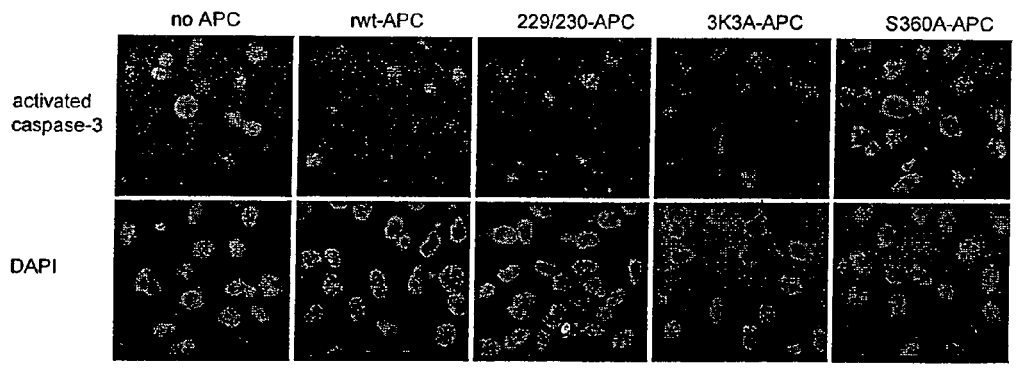

To determine cytoprotective activity of these APC variants, staurosporine-induced endothelial cell apoptosis (Joyce et al., supra, 2001; Mosnier and Griffin, supra, 2003) was studied. APC-mediated inhibition of staurosporine-induced apoptosis is time-dependent and dose-dependent and it requires APC's active site, PAR-1 and EPCR (Mosnier and Griffin, supra, 2003). Half-maximum inhibition of staurosporine-induced apoptosis by rwt-APC was achieved at 0.16 nM under the conditions employed (FIG. 4a). Dose-dependent inhibition of apoptosis by RR229/230AA-APC and KKK191-193AAA-APC was indistinguishable from that of rwt-APC with half-maximum inhibition at 0.17 nM and 0.14 nM, respectively (FIG. 4a). No inhibition of apoptosis by an APC mutant lacking the active site serine, S360A-APC (Gale et al., supra, 1997), was observed (FIG. 4a-c). The ability of rwt-APC and APC variants to inhibit generation of activated caspase 3 in endothelial cells exposed to staurosporine was monitored immunohistochemically. rwt-APC and the variants, RR229/230AA-APC and KKK191-193AAA-APC, each similarly reduced activated caspase-3-positive cells by approximately 70%, whereas the active site mutant, S360A-APC, had no effect (FIG. 4b-c). Thus, certain protease domain residues essential for normal anticoagulant activity of APC, namely Arg229 and Arg230 and Lys191, Lys192 and Lys193, are not required for normal anti-apoptotic activity of APC.

Figure 5:
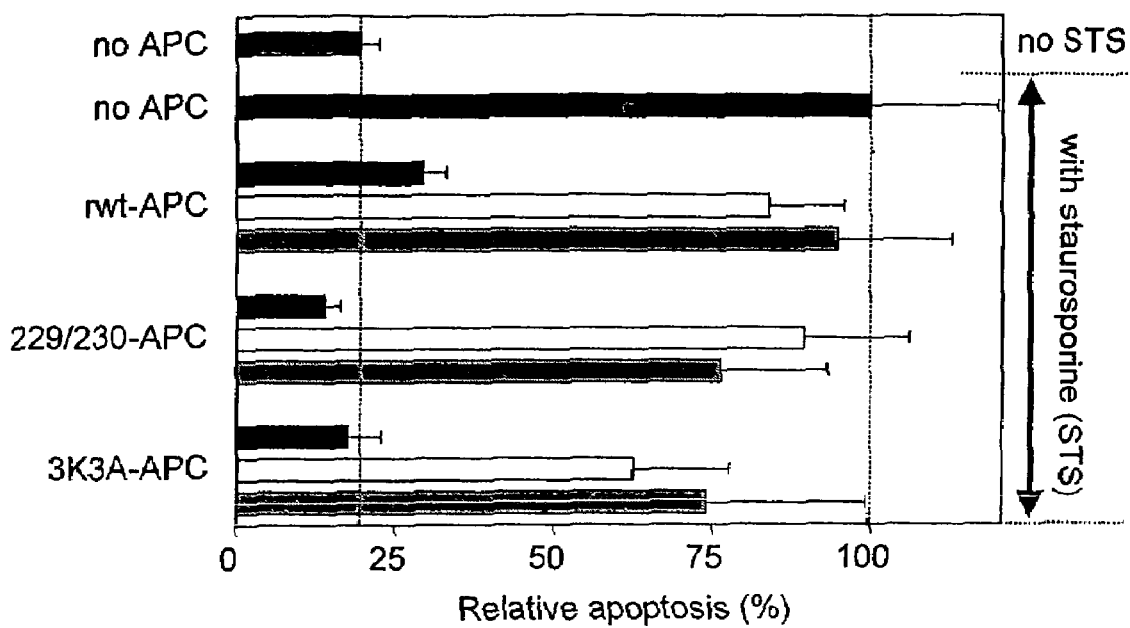
FIG. 5: Inhibition of apoptosis by rwt-APC and APC variants requires PAR-1 and EPCR. PAR-1 and EPCR-dependence for inhibition of staurosporine-induced endothelial cell apoptosis by rwt-APC and anticoagulantly impaired APC variants was studied using blocking antibodies against PAR-1 (open bars) (combination of WEDE-15 at 20 μg/ml and ATAP-2 at 15 μg/ml) or EPCR (cross-hatched bars)(rabbit anti-EPCR at 20 pg/ml). Solid bars represent "no antibodies added". Cells were incubated with rwt-APC or APC variants (5 nM) 5 h prior to induction of apoptosis by staurosporine (10 μM, 1 h). Apoptosis was analysed by the uptake of Apopercentage dye and expressed as a percentage relative to the percentage of apoptotic cells observed in the absence of added APC (20% of all cells), which was set as 100%. The bar with "vertical lines" represents relative apoptosis in the absence of APC and staurosporine. Each bar represents the mean±S.E.M. from at least three independent experiments.

APC anti-apoptotic effects require PAR-1 and EPCR (Cheng et al., supra, 2003; Mosnier and Griffin, supra, 2003). Similarly, the anti-apoptotic activity of RR229/230AA-APC and KKK191-193AAA-APC in assays of staurosporine-induced endothelial cell apoptosis required PAR-1 and EPCR because the cytoprotective activity of each APC variant was inhibited by 72% and 69% in the presence of antibodies against EPCR that block binding of APC to the receptor and by 88% and 55% in the presence of blocking anti-PAR-1 antibodies, respectively (FIG. 5). These results indicate that interactions between cells and the two APC variants, like rwt-APC, require PAR-1 and EPCR.

Cleavage of Synthetic PAR-1 N-terminal Tail by Wild Type and Variant APC's

Figure 6:
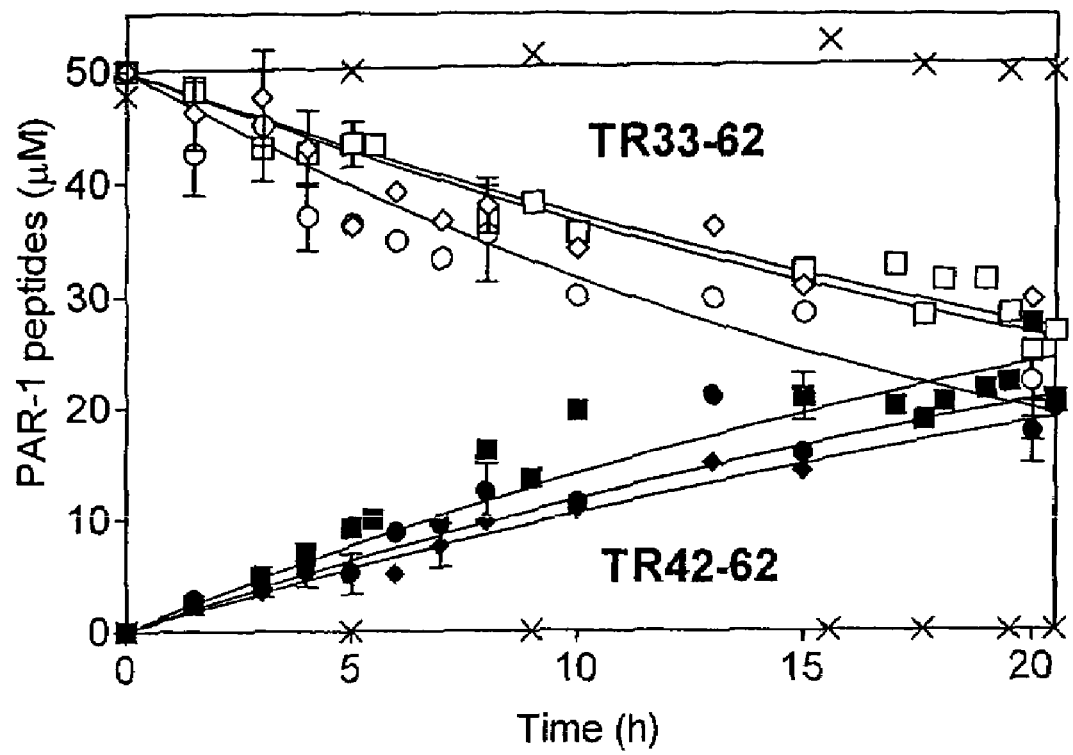
FIG. 6: Cleavage of PAR-1 N-terminal TR33-62 peptide at Arg41 by rwt-APC and APC variants. HPLC was used to monitor TR33-62 cleavage by APC over time as disappearance of the TR33-62 peptide substrate peak (open symbols) and as appearance of the TR42-62 peptide product peak (solid symbols). Symbols denote: ■,□: rwt-APC; •,○: RR229/230AA-APC; ◆,◇: KKK191-193AAA-APC and X,X: S360A-APC. The pooled data points of 3-5 independent experiments are shown for rwt-APC and the two anti-apoptotic APC variants. No cleavage was observed for the S360A-APC that lacks the active site Ser (X). Error bars indicate±S.E.M.

The absence of anti-apoptotic activity of S360A-APC and the requirement for PAR-1 imply that a primary mechanistic step for APC's anti-apoptotic activity involves PAR-1 proteolytic activation (Cheng et al., supra, 2003; Mosnier and Griffin, supra, 2003). To characterize the effects of the mutations in APC on proteolytic activation of PAR-1 due to cleavage at Arg41, a synthetic 30-mer peptide representing the PAR-1 N-terminal sequence (residues 33-62 (TR33-62)) was studied as an APC substrate. This TR33-62 PAR-1 peptide is cleaved at Arg41 by thrombin (Arosio et al., supra, 2000). APC cleaves another PAR-1 synthetic N-terminal peptide at Arg41, the thrombin cleavage site (Kuliopulos et al., supra, 1999). Using HPLC quantitative analysis, we found that rwt-APC cleaved the TR33-62 peptide at Arg41 and generated similar fragments as thrombin, TR33-41 and TR42-62, but at approximately a 25,000-fold lower catalytic efficiency based on comparison of $k_{cat}/K_m$ for the two enzymes (data not shown). When the time course for TR33-62 cleavage was monitored using HPLC to quantify the disappearance of the peak for the TR33-62 substrate and the appearance of the TR42-62 product, the results showed that there were no substantial differences in the rate of TR33-62 cleavage between the rwt-APC, RR229/230AA-APC and KKK191-193AAA-APC (FIG. 6). Similarly, no significant differences in APC-induced $Ca^{++}$-intracellular flux monitored as FURA-2-AM fluorescence changes were observed in EA.hy926 endothelial cells when rwt-APC was compared with the two anti-apoptotic APC variants, RR229/230AA-APC and KKK191-193AAA-APC (data not shown). These results are consistent with the hypothesis that APC cleaves PAR-1 at Arg41 and that the mutations in the two APC variants described here with reduced anticoagulant activity but with normal anti-apoptotic activity did not significantly reduce the ability of the protease domain of APC to cleave PAR-1 at Arg41.

In summary, to generate recombinant APC variants with reduced risk of bleeding due to reduced anticoagulant activity, we dissected APC's anticoagulant activity from its cytoprotective activity by site-directed mutagenesis. Using staurosporine-induced endothelial cell apoptosis assays, we show here that Ala mutations (RR229/230AA and KKK191-193AAA) in two APC surface loops that severely reduce anticoagulant activity result in two APC variants that retain normal anti-apoptotic activity that requires protease activated receptor-1 and endothelial cell protein C receptor. Moreover, these two APC variants retain a normal ability to cleave a PAR-1 N-terminal peptide at Arg41. To compare these two APC variants to rwt-APC in terms of their relative anti-apoptotic and anticoagulant activities (determined by APTT; note in table 1 anticoagulant activity was determined by dilute PT), we assigned the observed activity of rwt-APC a value of 100% and calculated the percent activity of each APC variant from dose-response data (FIGS. 3 and 4). This normalization inherently yields a "cytoprotective to anticoagulant" ratio for rwt-APC of 1.0 (Table 2). When the ratio of anti-apoptotic activity to anticoagulant activity was calculated for the APC mutants (Table 2), the two APC variants exhibited 7-times and 25-times greater anti-apoptotic activity relative to anti-coagulant activity compared to rwt-APC, respectively. These ratios are similar to the values seen in Table 1 calculated using the dilute PT assay for anticoagulant activity.

Thus, these data imply that the RR229/230AA and KKK191-193AAA mutations in APC which cause decreased cleavage at Arg506 in factor Va do not impair cleavage at Arg41 in PAR-1.

The references and patents cited herein, are hereby incorporated by reference in their entirety.

We Claim:

1. A method of protecting cells against damage caused at least in part by apoptosis, comprising administering to a subject or to cells a therapeutic dose of a recombinant activated protein C mutant, wherein said recombinant activated protein C mutant is KKK191-193AAA-APC relative to SEQ ID NO:15.

2. The method of claim 1, wherein the dose is between about 0.01 mg/kg/hr to about 1.1 mg/kg/hr, continuous infusion for about 4 hours to about 96 hours.

3. The method of claim 1 wherein the cells are selected from the group consisting of brain cells, heart cells, kidney cells, lung cells, liver cells, epithelial cells, and endothelial cells.

4. The method of claim 1, wherein said subject is at risk for cellular Damage to blood vessels or other organs caused at least in part by apoptosis.

5. The method of claim 4, wherein said risk for cellular damage is the result of any one or more of sepsis, ischemia/reperfusion injury, stroke, ischemic stroke, acute myocardial infarction, acute neurodegenerative disease, chronic neurodegenerative disease, organ transplantation, chemotherapy, and radiation injury.

6. The method of claim 5, wherein the chronic neurodegenerative disease is selected from the group consisting of Alzheimer's disease, Down syndrome, Huntington's disease, and Parkinson's disease.

7. A method of protecting cells against damage caused at least in part by apoptosis, comprising exposing said cells to a therapeutic amount of recombinant activated protein C, wherein said recombinant activated protein C has a mutation consisting of the substitution of lysine residues 191, 192, and 193 of the protease domain with alanine residues relative to SEQ ID NO:15.

8. The method of claim 7, wherein the cells are selected from the group consisting of brain cells, heart cells, kidney cells, lung cells, liver cells, epithelial cells, and endothelial cells.

9. The method of claim 7, wherein the dose is between about 0.01 mg/kg/hr to about 1.1 mg/kg/hr, continuous infusion for about 4 hours to about 96 hours.

10. A method of protecting cells against damage caused at least in part by apoptosis comprising administering to a human a therapeutic dose of the recombinant activated protein C mutant KKK191-193AAA-APC relative to SEQ ID NO:15.

11. The method of claim 10, wherein the dose is between about 0.01 mg/kg/hr to about 1.1 mg/kg/hr, continuous infusion for about 4 hours to about 96 hours.

12. The method of claim 10, wherein the cells are selected from the group consisting of brain cells, heart cells, kidney cells, lung cells, liver cells, epithelial cells, and endothelial cells.

13. The method of claim 10, wherein said human is at risk for cellular damage to blood vessels or other organs caused at least in part by apoptosis.

14. The method of claim 13, wherein said risk for cellular damage is the result of any one or more of sepsis, ischemia/reperfusion injury, stroke, ischemic stroke, acute myocardial infarction, acute neurodegenerative disease, chronic neurodegenerative disease, organ transplantation, chemotherapy, and radiation injury.

15. The method of claim 14, wherein the chronic neurodegenerative disease is selected from the group consisting of Alzheimer's disease, Down syndrome, Huntington's disease, and Parkinson's disease.

16. A method of protecting cells against damage caused at least in part by apoptosis comprising administering to a mammal a therapeutic dose of a recombinant activated protein C mutant that has a mutation consisting of the substitution of three contiguous lysine residues of loop 37 of the protease domain with three contiguous alanine residues relative to SEQ ID NO:15.

17. The method of claim 16, wherein the cells are selected from the group consisting of brain cells, heart cells, kidney cells, lung cells, liver cells, epithelial cells, and endothelial cells.

18. The method of claim 16, wherein the dose is between about 0.01 mg/kg/hr to about 1.1 mg/kg/hr, continuous infusion for about 4 hours to about 96 hours.

19. The method of claim 16, wherein said mammal is at risk for cellular damage to blood vessels or other organs caused at least in part by apoptosis.

20. The method of claim 19, wherein said risk for cellular damage is the result of any one or more of sepsis, ischemia/reperfusion injury, stroke, ischemic stroke, acute myocardial infarction, acute neurodegenerative disease, chronic neurodegenerative disease, organ transplantation, chemotherapy, and radiation injury.

21. The method of claim 20, wherein the chronic neurodegenerative disease is selected from the group consisting of Alzheimer's disease, Down syndrome, Huntington's disease, and Parkinson's disease.

* * * * *